United States Patent [19]
Forster et al.

[11] Patent Number: 5,974,867
[45] Date of Patent: Nov. 2, 1999

[54] METHOD FOR DETERMINING CONCENTRATION OF A LAMINAR SAMPLE STREAM

[75] Inventors: Fred K. Forster; Paul C. Galambos; Bernhard H. Weigl; Mark R. Holl, all of Seattle, Wash.

[73] Assignee: University of Washington, Seattle, Wash.

[21] Appl. No.: 08/961,345

[22] Filed: Oct. 30, 1997

Related U.S. Application Data

[60] Provisional application No. 60/049,533, Jun. 13, 1997.

[51] Int. Cl.⁶ .................................................. G01N 21/78
[52] U.S. Cl. .................... 73/61.41; 73/61.71; 422/82.05; 436/172
[58] Field of Search ................................ 73/53.01, 61.41, 73/61.43, 61.71; 422/82.05, 82.08, 81; 436/172, 52, 164

[56] References Cited

U.S. PATENT DOCUMENTS

| | | | |
|---|---|---|---|
| 5,716,852 | 2/1998 | Yager et al. | 436/172 |
| 5,773,298 | 6/1998 | Lynggard et al. | 436/52 |
| 5,780,754 | 7/1998 | Karlberg et al. | 73/864.81 |

FOREIGN PATENT DOCUMENTS

WO 97/00442  1/1997  WIPO.
WO 97/39338  10/1997  WIPO.

OTHER PUBLICATIONS

U.S. application No. 08/900,926, Weigl et al., filed Jul. 25, 1997.
U.S. application No. 08/829,679, Weigl et al., filed Mar. 31, 1997.
U.S. application No. 08/663,916, Yager et al., filed Jun. 14, 1996.
U.S. application No. 08/625,808, Weigl et al., filed Mar. 29, 1996.
Arquint, P. et al. (1994), "Micromachined Analyzers on a Silicon Chip," *Clin. Chem.* 40/9:1805–1809.
Fuh, C.B. and Giddings, J.C. (1995), "Isolation of Human Blood Cells, Platelets, and Plasma Proteins by Centrifugal SPLITT Fractionation," *Biotechnol. Prog.* 11:14–20.
Fuh, C.B. et al. (1993), "Rapid Diffusion Coefficient Measurements Using Analytical SPLITT Fractionation: Applications to Proteins," *Analytical Biochemistry* 208:80–87.
Galambos, P. et al. (1997), "A Method for Determination of pH Using a T–Sensor," 1997 International Conference on Solid State Sensors and Actuators (Transducers '97), Chicago, IL, Jun. 16–19, 1:535–538.
Jacobsen, S.C. et al. (1994), "Microchip Capillary Electrophoresis with an Integrated Postcolumn Reactor," *Anal. Chem.* 66:3472–3476.
Weigl, B. et al. (1996), "Diffusion–Based Optical Chemical Detection in Silicon Flow Structures," Analytical Methods & Instrumentation, Special Issue µTAS 96:174–184.

*Primary Examiner*—Michael Brock
*Attorney, Agent, or Firm*—Greenlee, Winner and Sullivan, P.C.

[57] ABSTRACT

Methods and apparatuses including programmed computers are provided for determining the initial concentration of diffusible particles in a sample stream introduced into a system wherein the sample stream which contains the diffusible particles flows in adjacent laminar flow with an indicator stream containing an indicator substance capable of exhibiting an observable change at a known concentration of the diffusible particles.

18 Claims, 6 Drawing Sheets

METHOD FOR DETERMINING CONCENTRATION OF A LAMINAR SAMPLE STREAM

CROSS-REFERENCE TO RELATED APPLICATIONS

This is a utility patent application taking priority from provisional patent application 60/049,533 filed Jun. 13, 1997, fully incorporated herein by reference to the extent not inconsistent herewith.

This invention was made with government support by the Department of the Army. The government has certain rights in the invention.

BACKGROUND OF THE INVENTION

Chemical analysis of small samples is important in the fields of environmental science, chemical process control, biotechnology and medicine. In particular, the desire to make medical diagnoses at the point of care is driving the development of devices that can make accurate clinical chemical analyses of very small samples. The concept of a laboratory on a chip (LOC), incorporating small-scale versions of many chemical analysis devices (e.g., separators, reactors, detectors) onto a single silicon chip (Jacobsen, S. C. et al. [1994], "Microchip capillary electrophoresis with an integrated postcolumn reactor," *Anal. Chem.* 66:3472–3476), is an active area of development.

The goal of chemical analysis is often to determine the concentration of constituents in a sample. The separation of the constituent of interest from interfering species is required before accurate concentration measurements can be made. In LOC devices, sample volumes are small (e.g. 100 nl). An effective method of constituent separation for such small samples is electrophoresis (Jacobsen et al., supra). Electrophoresis separates constituents axially along a flow channel due to differences in constituent mobilities. Species detection and concentration measurement is accomplished downstream of constituent separation in the same channel.

Small-scale separation techniques include split-flow thin (SPLITT) fractionation techniques (Fuh, C. B. and Giddings, J. C. [1995], "Isolation of human blood cells, platelets, and plasma proteins by centrifugal SPLITT fractionation," *Biotechnol. Prog.* 11:14–20; and Fuh, C. B. et al. [1993], "Rapid diffusion coefficient measurements using analytical SPLITT fractionation: applications to proteins," *Analytical Biochemistry* 208:80–87). These techniques involve substantially larger flow rates than the preferred devices used in the present invention.

A different, smaller-scale approach to constituent separation based on a T-sensor is described in Weigl et al., U.S. patent application Ser. No. 08/829,679 filed Mar. 31, 1997, PCT Application No. PCT/US97/05245 filed Mar. 31, 1997, and U.S. patent application Ser. No. 08/625,808 filed Mar. 29, 1996, all of which are incorporated herein by reference to the extent not inconsistent herewith.

A T-sensor operates by bringing a sample stream and an indicator stream into contact in a single channel. As constituents diffuse from the sample stream they react with a constituent in the indicator stream to produce a complex or change which can be detected, preferably by optical methods. A means for using this type of signal to determine the initial concentration in the sample of such constituents is needed rather than using a downstream detector as in Jacobsen et al., supra.

A device related to the T-sensor is the microscale diffusion-based separator described in Yager et al., U.S. patent application Ser. No. 08/663,916 filed Jun. 14, 1996 and PCT Publication No. WO 9700442 published Jan. 3, 1997, incorporated herein by reference to the extent not inconsistent herewith.

Publications containing subject matter by inventors hereof include Weigl, B. et al. (1996), "Diffusion-Based Optical Chemical Detection in Silicon Flow Structures," *Analytical Methods & Instrumentation*, Special Issue MTAS 96:174–184; and Galambos, P. et al. (1997), "A method for determination of pH using a T-sensor," 1997 International Conference on Solid State Sensors and Actuators (Transducers '97), Chicago, Ill., June 16–19, 1:535–538.

Means for determining initial concentrations of constituents in sample streams entering such devices is also needed.

All references discussed herein are hereby incorporated by reference in their entirety, to the extent not inconsistent herewith, particularly with respect to the teachings of art-known devices and procedures.

SUMMARY OF THE INVENTION

This invention provides methods for generating calibration models, i.e. reference data, relating (a) positions of points of known concentration of diffusible particles in an indicator stream in laminar flow in a substantially rectangular flow channel with a sample stream to (b) initial concentrations of said particles in said sample stream. For example, the hydrogen or sodium ion content of blood may be used to generate the model.

The models are capable of taking into account differing physical properties of each stream, i.e., differing flow rates, differing viscosities and different diffusivities of analyte (diffusible) particles in each stream. The model comprises a set of reference data which can be applied to test systems having different parameters. It is not necessary to know the viscosities of the two streams, nor is it necessary to control the flow rates to generate the analytical model or to use it to determine initial sample concentration. However, the flow rate ratio must be known, i.e., by measurement, or by calculation from the pressure drop along the inlet channels (if the viscosities of the streams are not known), if the flow rates are not controlled to be a predetermined value.

The sample stream may be any stream containing particles of the same or different size, for example blood or other body fluid, contaminated drinking water, contaminated organic solvents, urine, biotechnological process samples, e.g. fermentation broths, and the like. The diffusible particles may be any smaller particles in the sample stream which are capable of diffusing into the indicator stream in the flow channel, e.g. hydrogen, calcium or sodium ions, proteins, e.g. albumin, organic molecules, drugs, pesticides, and other particles. In the preferred embodiment when the sample stream is whole blood, small ions such as hydrogen and sodium diffuse rapidly across the channel, whereas larger particles such as those of large proteins diffuse slowly. Blood cells do not diffuse. Preferably the diffusible particles are no larger than about 3 micrometers, more preferably no larger than about 0.5 micrometers, or are no larger than about 1,000,000 MW, and more preferably no larger than about 50,000 MW.

The indicator stream introduced into laminar flow in the flow channel with the sample stream comprises a liquid carrier containing an indicator substance. The liquid carrier can be any fluid capable of accepting particles diffusing from the feed stream and containing an indicator substance. Some diffusing particles may cause a detectable change directly in the indicator stream without the necessity for a separate substance used as an indicator substance. Preferred indicator streams comprise water and isotonic solutions such as salt water with a salt concentration of about 10 mM NaCl, KCl or MgCl, or organic solvents like acetone, isopropyl alcohol, ethanol, or any other liquid convenient which does not interfere with the effect of the analyte (diffusible particles) on the indicator substance or detection means.

The indicator substance is preferably a substance which changes in fluorescence or color in the presence of analyte particles, such as a dye, enzymes, and other organic molecules that change observable properties as a function of concentration of the diffusible particles.

The system containing the laminar flow channel used for generating the calibration model can be any system providing a flow channel small enough to allow for adjacent laminar flow of the sample and indicator streams. One such system is shown in FIG. 1. Other such systems include the diffusion-based separator described in PCT Publication No. WO 9700442 published Jan. 3, 1997 incorporated herein by reference to the extent not inconsistent herewith, or other SPLITT devices allowing for laminar flow as discussed above. The aspect ratio $a_R$ of the flow channel is defined as b/h where 2h is the dimension of the flow channel in the direction that crosses the boundary between the sample and indicator streams and where 2b is the dimension of the flow channel in the other, transverse direction. Regardless of the aspect ratio, the analyte in the sample stream enters the flow channel with a concentration that is uniform in the b-direction. Thus regardless of the aspect ratio, the primary diffusion direction is in the h-direction, and the model is applicable to aspect ratios both small, medium and large. However, for optical access, the preferred aspect ratio is less than about ¼ and more preferably less than about ⅛.

The flow channel is preferably comprised in a microfabricated channel cell such as that described in PCT Application No. PCT/US 97/05245 incorporated herein by reference to the extent not inconsistent herewith. The channel cell may be fabricated by microfabrication methods known to the art, e.g. methods comprising forming channels in a silicon microchip, such as by etching grooves into the surface of the silicon microchip and placing a glass cover over the surface. Precision injection molded plastics may also be used for fabrication.

The calibration models of this invention are used by detecting the position within the laminar flow channel of diffusible particles from a sample stream which diffuse into an indicator stream until they are present at a sufficient concentration to cause an observable change (i.e. a change detectable by any means including the naked eye and other instruments such as fluorescence detectors) in an indicator substance in the indicator stream. This detectable change will form an isoconcentration line (also referred to herein as an "isoconcentration curve") in the indicator stream. The physical location of this isoconcentration curve in the flow channel for a given analyte stays the same over time as long as the flow speed is constant and the sample unchanged.

The calibration models are used to determine the initial concentration of such diffusible analyte particles in a test sample stream in the same type of system whose parameters were used to calculate the model. The system used to determine unknown initial concentrations in test sample streams should be identical or substantially identical to a system having parameters used to generate the calibration model. By substantially identical is meant that at least the dimensions of the flow channels, the flow rates of each stream, and the composition of the indicator stream should be the same in each system.

The term "length" (L) used herein with respect to a flow channel refers to the direction of flow. The channel dimension in the direction of particle diffusion (d) is termed "depth" herein. The channel dimension in the direction at right angles to both the length and depth is called the "width" (w).

The term "particles" refers to molecules, cells, large molecules such as proteins, small molecules comprised of one or several atoms, and ions. The particles may be suspended or dissolved in the stream. The term "stream" refers to a carrier fluid such as water or other liquid, air or other gas, containing desired and/or undesired particles. The term "particles" as used herein does not include the molecules of the carrier stream. Other physical quantities which act like particles in systems as described herein, e.g., temperature, are also included within the definition of "particles" herein.

The term "laminar flow" of two streams means stable, side-by-side, non-recirculating, flow of two streams without mixing. There is no turbulence and zones of recirculation are negligible. As is known to the art, the Reynolds number of a flow is the ratio of inertial forces to viscous forces. The Reynolds number of the system is preferably less than 1. For flow through a duct, the Reynolds number is calculated using the equation $Re = \rho Dh(U/\mu)$ where Re is the Reynolds number, $\rho$ is the mass density of the fluid, Dh is the hydraulic diameter of the duct, U is the mean velocity over the duct cross-section, and $\mu$ is the absolute viscosity of the fluid.

As the Reynolds number is reduced, flow patterns depend more on viscous effects and less on inertial effects. Below a certain Reynolds number, inertial effects are insufficient to cause phenomena indicative of their significant presence such as laminar recirculation zones and turbulent flow. Therefore, non-turbulent, laminar non-recirculating flow occurs in the extraction devices discussed herein. This allows two laminar non-recirculating fluid streams to flow down a channel for the purpose of diffusion of analyte particles from the sample stream to the indicator stream.

A method of this invention for determining the initial concentration of diffusible analyte particles in a sample stream entering a laminar flow channel of known dimensions in laminar flow with an indicator stream containing an indicator substance capable of exhibiting a detectable change at a known concentration of said diffusible analyte particles, comprises:

(a) determining the flow rate ratio of said streams and diffusivity ratio of said analyte particles in said streams;

(b) selecting detection points in said indicator stream where said indicator substance exhibits a detectable change indicative of a particular concentration of said diffusible analyte particles at said detection point;

(c) using said known concentration of diffusible analyte particles at said detection points and the locations of said detection points to determine, preferably by calculation, the initial concentration of said diffusible analyte particles in said sample stream.

The flow rates may be determined by controlling the streams to flow at a particular known value or by measuring the flow rates by means known to the art. Diffusivities may be determined by reference to published tables.

The accuracy of the method is improved by selecting a plurality (two or more, more preferably three or more, and most preferably about nine) of detection points in said indicator stream.

The accuracy of the method is also improved in cases where the indicator substance is diffusible in the sample stream by including in the method steps including determining the diffusivity of the indicator substance in the sample stream, determining the local concentration of the indicator substance at each of the detection points and using the local concentrations of indicator substance to calculate the concentrations of the diffusible analyte particles at each of the detection points.

The viscosities of the sample and indicator streams may be substantially equal, such that the viscosities do not appreciably affect the flow rates of the sample and indicator streams, or they may be different. The flow rates of each stream may also be the same or different, but in any case, the flow rates of each stream must be known.

Where the viscosities of the two streams are different, their viscosity ratio must either be known or must be determined, preferably by a method comprising determining the position of the interface between the sample stream and the indicator stream and using this information to calculate the viscosity ratio.

Preferably, the detectable change in the indicator substance is detected by an optical instrument. Specific response values of the optical instrument are correlated with (calibrated to) known concentrations of the analyte particles in the indicator stream.

Once the concentrations of analyte particles at selected locations in the indicator stream are known, the initial concentration of analyte particles in the incoming sample stream can be determined. Methods for calculating initial concentrations are provided herein. Initial concentration of analyte particles in the incoming sample stream may also be determined by reference to a previously-generated database containing data relating incoming sample stream analyte concentration to concentration of analyte particles at selected location(s) in the indicator stream tested under a number of different conditions of flow rate, type of particle, type of carrier stream, channel dimensions, viscosities and diffusivities. The latter approach requires all combinations of the above parameters expected in an actual sample case.

A method is also provided herein for determining the viscosity of a first stream in laminar flow relative to a second stream in a laminar flow channel, comprising:
(a) determining the flow rates of said first and second streams;
(b) determining the centerline of said flow channel;
(c) determining the position of the interface between said first and second streams in said flow channel with respect to said centerline;
(d) calculating the viscosity ratio of said first stream to said second stream using values determined in steps (a), (b), and (c).

Analytical models may be prepared which are useful for determining the initial concentration of diffusible analyte particles in test sample streams by generating reference data relating positions of points of known concentration of diffusible analyte particles in an indicator stream comprising an indicator substance capable of exhibiting a detectable change at a known concentration of said diffusible analyte particles, in laminar flow with a sample stream in a flow channel having known dimensions, to initial concentrations of said analyte particles in said sample stream. The reference data may be generated by:
(a) providing flow rates for said streams and diffusivities of said analyte particles in said streams;
(b) providing a concentration of said analyte particles in said indicator stream correlated to a specific detectable change in said indicator substance;
(c) calculating the positions of points of said specific detectable change in said indicator substance which would result from different initial concentrations of said analyte particles in said sample stream.

In addition, the reference data may be generated by a method taking into account diffusion of the indicator substance into the sample stream by a method comprising providing the diffusivity of the indicator substance into the sample stream, the concentration of the indicator substance at various locations in the indicator stream, and the relationship of the points of detectable change in the indicator substance correlated with analyte particle concentration to varying indicator substance concentration in the indicator stream.

Further, the reference data may be generated by a method taking into account differing viscosities and/or flow rates of the sample and indicator streams.

After the reference data has been generated, it may be used to determine the initial concentration of diffusible analyte particles having diffusivities as provided above, in a test sample stream by:
(a) introducing said test sample stream and said indicator stream into a laminar flow channel of said known dimensions in laminar flow with an indicator stream at said flow rates provided above;
(b) detecting the position of at least one point of detectable change of said indicator substance in said indicator stream;
(c) comparing the detected position of step (b) with said reference data to determine the initial concentration of said diffusible analyte particles in said test sample stream corresponding to said detected position.

Apparatuses are also provided herein for determining the initial concentration of diffusible analyte particles in a sample stream comprising:
(a) a laminar flow channel of known dimensions for introduction of said sample stream in laminar flow with an indicator stream containing an indicator substance capable of exhibiting a detectable change at a known concentration of said diffusible analyte particles;
(b) means for determining the flow rates of said streams in said flow channel whereby said flow rates are known;
(c) means for detecting a change in said indicator substance at a selected detection point of known coordinates in said indicator stream, said change being indicative of a particular concentration of said diffusible analyte particles at said detection point;
(d) computerized means for calculating the initial concentration of said diffusible analyte particles in said sample stream using said known channel dimensions, known flow rates, and known coordinates.

The means for determining the flow rates of the streams in the laminar flow channel may be any means known to the art for directly detecting such flow rates, including means such as visible beads introduced into the flowing streams which may be observed at the beginning and end of a known distance, and means such as a stopwatch or other means known to the art for timing the travel of such beads, pressure sensors, and other means known to the art, including means for controlling the flow rates such as metered pumps or tubes providing a controlled amount of pressure.

The means for detecting the change in the indicator substance may be any means known to the art including optical sensors as described herein, heat sensors, and others.

The computerized means for calculating viscosity may comprise any processor programmed to perform the calculations described herein.

Also provided herein is an apparatus for determining the viscosities of two streams in parallel laminar flow in a laminar flow channel comprising:

(a) means for determining the flow rates of said streams;

(b) means for determining the distance of the interface between said streams in said flow channel from the centerline thereof;

(d) computerized means for calculating the viscosities of said streams using values determined in steps (a) and (b).

The means for determining the distance of the interface between the two streams from the centerline of the flow channel include means such as rulers, calipers and optical measurement devices known to the art, present marks on the flow channel indicating the centerline, and other means known to the art including dyes added to one or both streams to facilitate detection of the interface.

The computerized means for calculating the viscosities of the streams include any processors known to the art programmed to perform the calculations described herein.

A more detailed method for generating a calibration model of this invention which takes into account differing viscosities and flow rates for the two streams comprises:

(a) providing the following input information related to a system comprising a sample stream containing diffusible particles in laminar flow in a substantially rectangular flow channel, with an indicator stream containing an indicator substance capable of exhibiting an observable change at a known concentration of the diffusible particles:

(1) ratio of flow rate of the sample stream to the indicator stream;

(2) ratio of diffusivity of said particles in the sample stream to diffusivity of said particles in the indicator stream;

(3) half the channel depth (diffusion direction);

(4) position of interface between the indicator and sample streams and distance of the interface from the centerline or, alternatively, viscosities of the two streams;

(5) concentration of said particles causing the indicator substance in the indicator stream to make an observable change;

(b) calculating the positions of points of observable change in the indicator substance which would result if differing initial concentrations of the particles in the sample stream were used in the system.

It is not necessary to obtain the information for calculating the models from an actual physical system. Various possible values for the input data can be arbitrarily assigned, so that the models can generate reference data for a large number of possible system parameters. If the viscosities are not known, arbitrary values for the position of the interface can be assigned. Alternatively, an actual physical system can be used and the position of the interface observed. When an actual rather than a hypothetical system is used to provide input data for calculating the models, the initial concentration of the sample stream, if known, and the position of the actual isoconcentration line observed at points where the indicator substance exhibits a detectable change, can be used to check and validate the calculated data.

Preferably, the methods are performed using a computer to make the calculations, using as input the above described information.

As exemplified herein, the methods may be used to determine hydrogen ion concentration (pH) in both buffered and unbuffered systems. The methods may also be used for determining initial concentrations of other diffusible particles, including, but not limited to, electrolytes, proteins, enzymes, drugs, hormones, toxins, bacteria, viruses and diffusible cells. Preferred sample streams are physiological fluids such as blood, plasma, cerebrospinal fluid and urine.

Preferably, the method of determining the initial concentration of a test sample stream having an unknown concentration of diffusible particles is performed by computer.

DETAILED DESCRIPTION OF PREFERRED EMBODIMENTS

Symbols and abbreviations used in the following discussion are as follows:

$a_R$ Aspect ratio 2b/2h b Half-channel width (m) in y-direction c(x,z) Concentration (M)

$c_{dye}$ Concentration of indicator dye in indicator stream $c_{eq}$ Equilibrium concentration (M)

$c_o$ Entering sample concentration (M)

D Diffusivity (m$^2$/s)

$D_h$ Hydraulic diameter 4bh/(b+h)

dP/dx Pressure gradient (Pa/m) in flow direction h Half-channel depth (m) in z-direction I Intensity $$k \quad \sqrt{\frac{Pe_2}{Pe_1}}$$

[OH$^-$] Hydroxide ion concentration (M)

P Pressure in flow channel (Pa)

Pe Peclet number Uh/D q Volume flow rate (m$^3$/s)

u Fluid axial velocity (m/s)

U Average Velocity (m/s)

v Transformed fluid axial velocity (m/s)

w Optical path length x Axial distance coordinate (m)

$\tilde{x}$ x/h y Width coordinate z Cross-stream coordinate from interface into indicator stream (m)

$\tilde{z}$ z/h

α Interface offset from centerline normalized by h $\beta_1$ 1−α

$\beta_2$ 1+α

$\Gamma$ $c_{eq}/c_o$

γ ($\tilde{x},\tilde{z}$) nondimensional concentration (c−$c_{eq}$)/$c_o$ $\lambda_n$ Eigenvalues μ Absolute viscosity (Pa·s)

The subscript "1" denotes the indicator stream. The subscript "2" denotes the sample stream.

Figure 1:
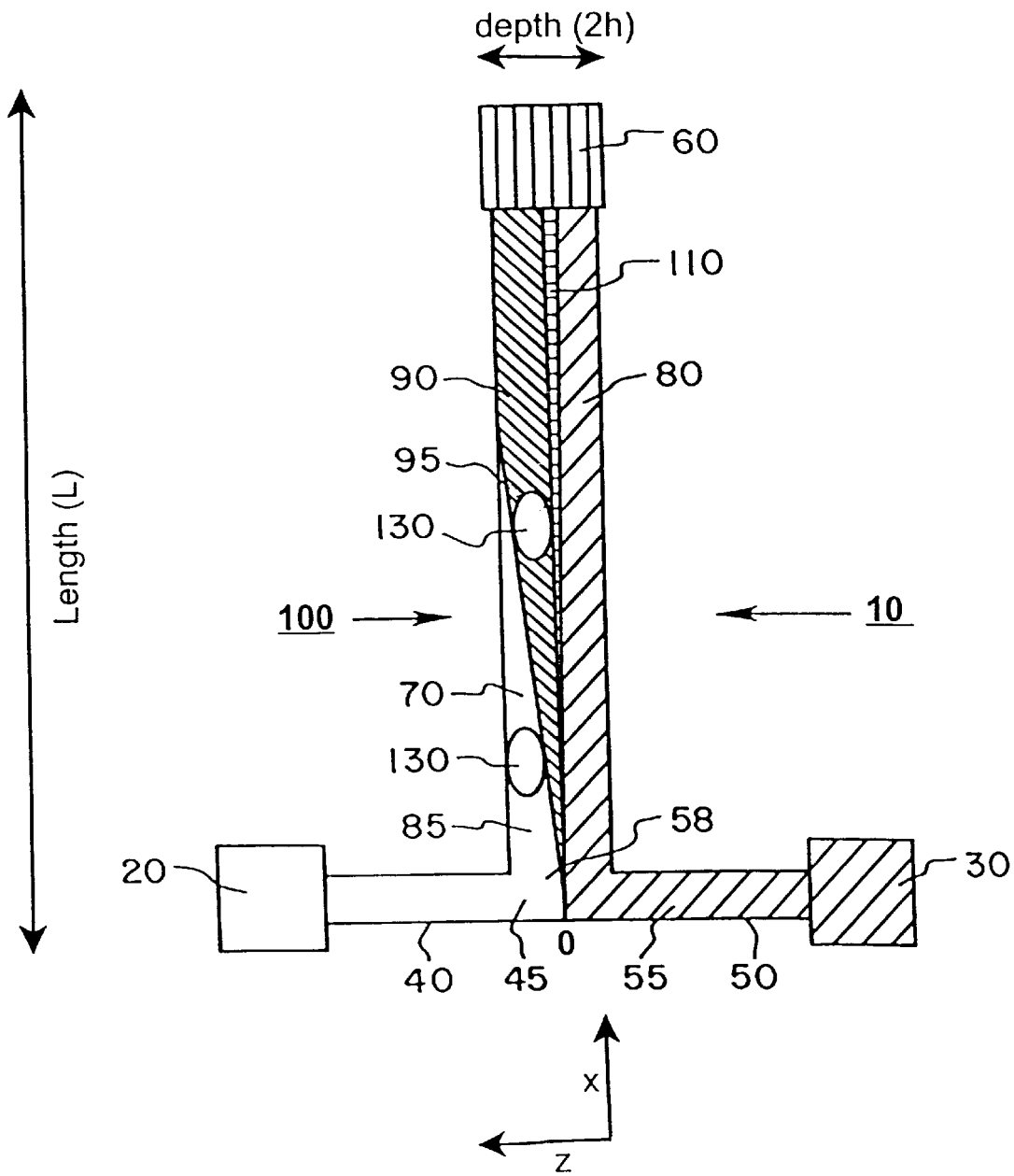
FIG. 1 shows a T-sensor device suitable for the practice of this invention.

A model-based method for the determination of constituent concentrations in flowing nanoliter volumes of liquid is presented. This method is exemplified using hydrogen ion concentration (pH measurement). A T-sensor as shown in FIG. 1 is used to bring sample fluid into contact with indicator fluid to produce low Reynolds number, laminar, co-flowing streams in a microchannel. By diffusion, the sample stream ions are brought into contact with the dye molecules in the indicator stream to produce an optically detectable signal.

As shown in FIG. 1, a channel cell in the form of a "T" is provided, referred to herein as T-sensor 10. The device can be microfabricated by etching on a silicon microchip. The input channels merge into laminar flow in a single flow channel, and all channels are sufficiently small that laminar flow is preserved for all operating conditions. In general, the Reynolds number of the system is less than 1. The sample containing small particles of interest, sample stream 80, is brought into the device through sample stream inlet port 30, from whence it flows into sample stream inlet channel 50, where it is referred to as sample inlet stream 55. An indicator stream 70 is brought into indicator stream inlet port 20, from whence it flows into indicator stream inlet channel 40, where it is referred to as indicator inlet stream 45.

Sample inlet stream 55 meets indicator inlet stream 45 at T-joint 58 at the beginning of flow channel 100, and the two streams flow in parallel adjacent laminar flow as indicator stream 70 and sample stream 80 to exit port 60. The indicator stream 70 contains an indicator substance such as a dye which reacts with diffusible analyte particles from the sample stream 80 by a detectable change in physical properties. Indicator stream 70 is shown in white in FIG. 1. Due to the low Reynolds number in the small flow channel 100, no turbulence-induced mixing occurs and the two streams flow parallel to each other without mixing. However, because of the short distances involved, diffusion does act in the h-direction perpendicular to the flow direction, so sample components (analyte particles) diffuse to the left into indicator stream 70. In the embodiment shown, the flow channel 100 is long enough so that analyte particles eventually become uniformly distributed across the width of flow channel 100 at uniform analyte particle diffusion area 120; however devices with shorter flow channels may also be used in this invention.

The indicator stream 70 flows into flow channel 100 to form an initial reference area 85 into which analyte particles have not yet diffused. Analyte particles from sample stream 80 diffusing into indicator stream 70 form an analyte detection area 90 where analyte particles create a detectable change in the indicator stream 70, preferably by causing a detectable change in property in an indicator substance within the indicator stream 70. Particles of an indicator substance, e.g. dye particles, may also diffuse into sample stream 80 to form a diffused indicator area 110. In some cases, e.g., Example 3 below, diffusion of the indicator substance into the sample stream is negligible and does not affect the calculation of the analytical model or its use. If a change in local concentration of the indicator substance is a problem in some applications due to diffusion of indicator substance into the sample stream, its diffusion rate can be made arbitrarily small by immobilization on polymers or beads, e.g. dextran or indicator beads 130 (not shown to scale). Alternatively, the analytical model can be modified to take such diffusion into account using the calculation methods described below to calculate the concentration of sample particles to calculate the concentration of indicator substance at the point where the detectable change takes place.

The analytical model may be used to calculate the ratio of the local concentration to the entering concentration for two or more diffusing indicator or analyte species. These local concentration calculations may be used with an observed optical signal indicating local concentration of analyte at a given location in the device to calculate the entering concentration of the analyte in the sample stream for cases where chemical reactions between species do not significantly alter the diffusion process (e.g., where there is an oversupply of one reacting constituent and the reaction does not affect the diffusion rate of the other reacting species).

In the laminar flow T-sensor 10 of FIG. 1, a sample stream 80, e.g. blood, and an indicator stream 70 containing an indicator dye are joined at the intersection of sample stream inlet channel 50 and indicator stream inlet channel 40, with flow channel 100 (i.e., T-joint 58) and flow next to each other in flow channel 100 until they exit the structure at exit port 60. Small ions such as $H^+$ and $Na^+$ diffuse rapidly across the diameter of flow channel 100, whereas larger ions such as the dye anion diffuse only slowly. Larger particles such as sugars, proteins, and the like and blood cells show no significant diffusion within the time the indicator stream 70 and sample stream 80 are in contact with each other. The smaller sample components diffuse more rapidly and equilibrate close to the T-joint 58, whereas larger components equilibrate further up in flow channel 100. Furthermore, as the indicator has a particular half-saturation concentration ($pK_a$, in the case of a pH dye), a front or detection area boundary 95, referred to herein as the observed isoconcentration curve, of indicator dye color or fluorescence change, exists as diffusion proceeds across the channel to form detection area 90. In practice the detection area boundary 95 and reference area 85 may form a curved line. Detectable changes in the indicator substance which occur as a result of concentration of analyte particles in the indicator stream may form a continuum such that, for example, a detection instrument could detect numerous different concentrations indicated by different signal intensities.

In a preferred embodiment, e.g., as described in Example 1, the detection instrument is calibrated to analyte concentration in the indicator stream.

Analytical models of the diffusion process that take into account the different physical properties of each stream, i.e. differing flow rates, differing viscosities, and different diffusivities of analyte particles and indicator substance are provided herein. The models also take into account the effects of ideal buffering to determine incoming sample stream pH.

As will be understood by those skilled in the art, sample concentration values determined by the model may be verified by comparison with calibration curves generated using sample streams having different concentrations of analyte and may be adjusted by means of constants or functions generated by such comparisons to compensate for variables not addressed by the models.

In FIG. 1, the x and z coordinates are shown with the x coordinate being in the axial or flow direction of the device extending positively from the origin 0 shown at the midpoint of the upstream end of flow channel downstream, and the z coordinate beginning at the interface between the two streams, shown in FIG. 1 as the origin 0 and extending positively in the direction of the indicator stream 70. The y coordinate is in the direction perpendicular to and into the plane of the figure.

Figure 2:
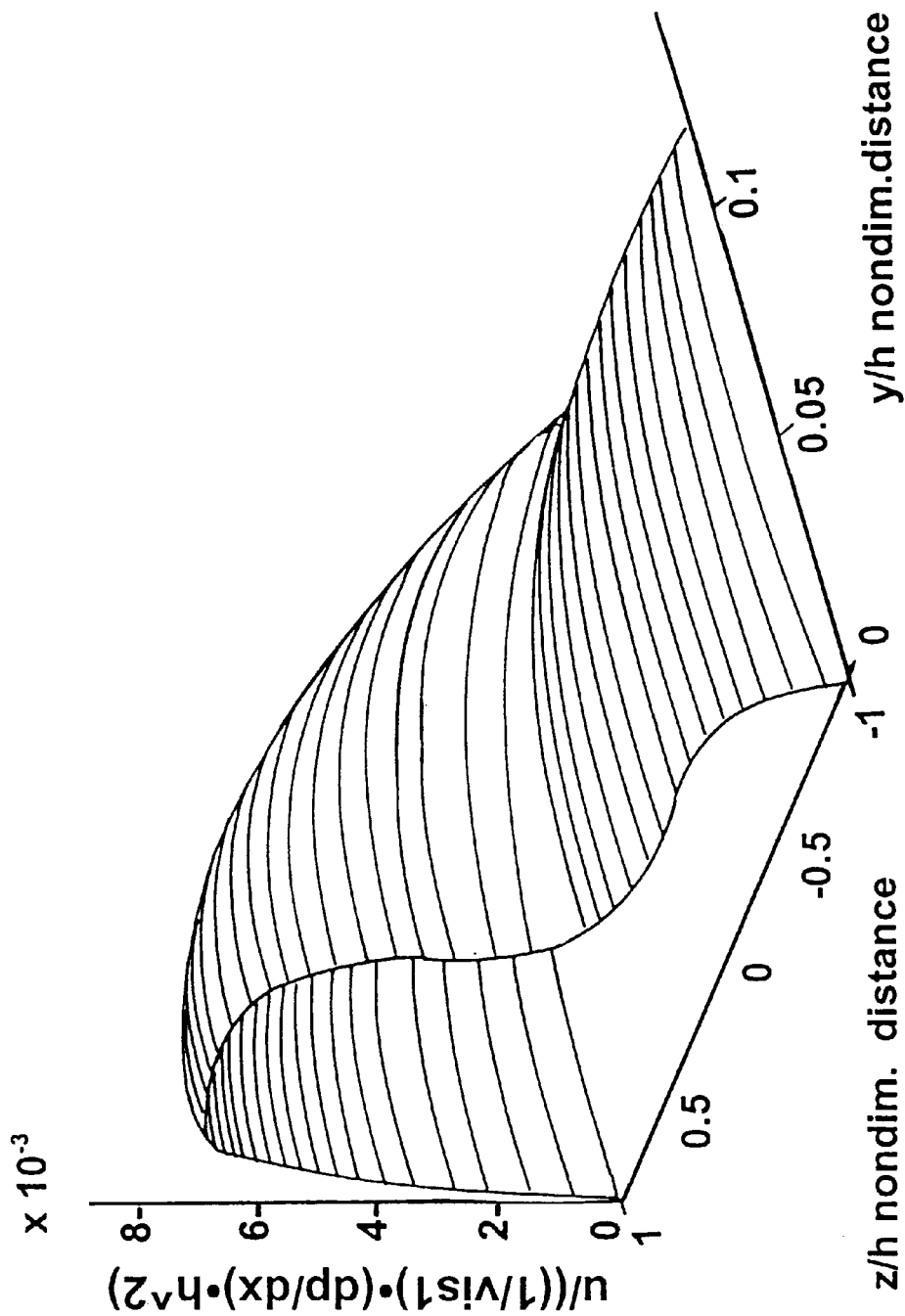
FIG. 2 is a three-dimensional velocity profile for two fluids of different viscosities flowing in a microchannel.

FIG. 2 is a three-dimensional graph showing the calculated velocity profile for fluids of two different vicsocities wherein the ratio of the viscosity of the indicator stream to the viscosity of the sample stream is 0.25, in a thin, narrow rectangular flow channel having an aspect ratio of ¼. The ratio of volume flow rate in the indicator stream to that in the sample stream is four. The z/h coordinate represents non-dimensional distance in the diffusion direction. The y/h coordinate represents non-dimensional distance in the width direction. The vertical coordinate is nondimensional fluid velocity.

FIG. 3 shows actual hydrogen ion concentration curves indicated by color changes in the indicator streams using buffered sample and unbuffered indicator streams as described in Example 2 below. The sample inlet stream 55 flows in from the right to contact the indicator inlet stream 45 at interface 120 which can be identified by an observable change in the indicator substance at the beginning of analyte detection area 90. In the flow channel, sample inlet stream 55 becomes sample stream 80 and indicator inlet stream 45 becomes indicator stream 70. The direction of flow is indicated by the white arrows.

Figure 3B:
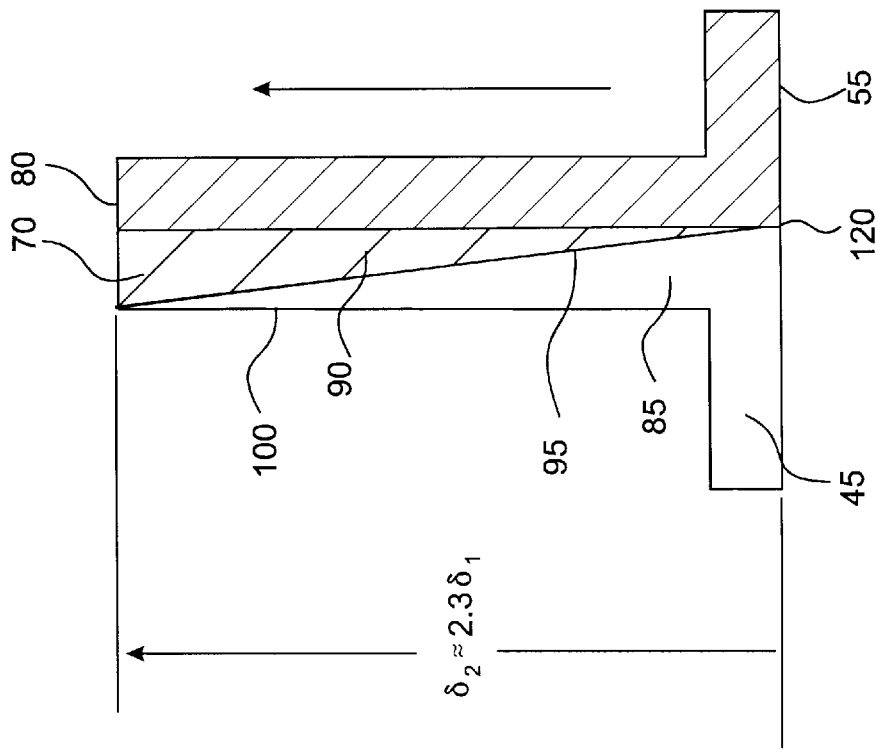
FIGS. 3A and 3B show actual hydrogen ion concentration curves indicated by color changes in the indicator stream using a buffered sample stream at pH 9.0 and a weakly buffered indicator dye stream (pH 5.0).
Figure 3A:
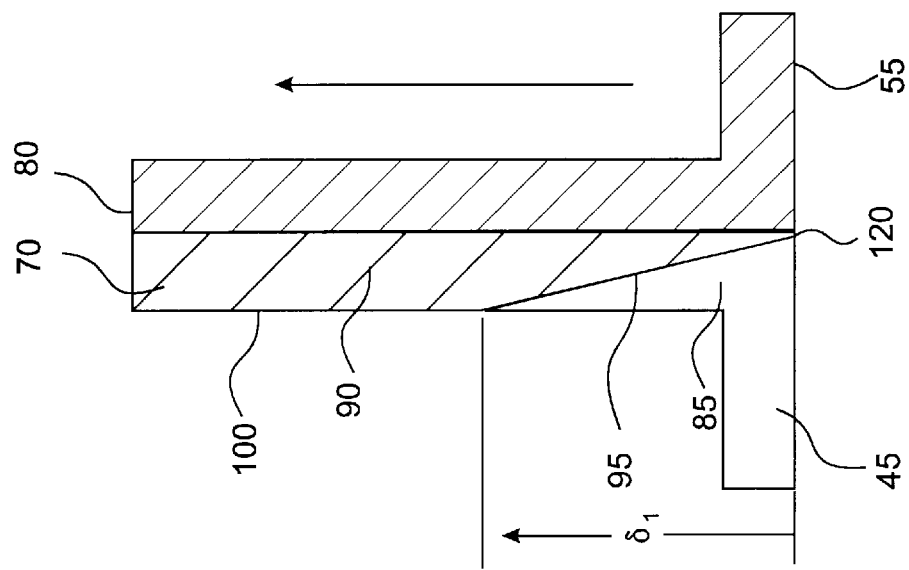

In FIG. 3A the T-sensor driven by a pressure differential of 30 mm water between both inlet ports and the outlet port, and in FIG. 3B, the same experiment is shown with a pressure differential of 70 mm water. The sample inlet stream 55 is a buffer solution of pH 9.0 (right inlet). A weakly buffered indicator dye solution (pH 5.0) enters as the indicator inlet stream 45 from the left. Note the distinct conversion of the dye from one form to the other as diffusion proceeds caused by dye dynamic range saturation.

In both FIG. 3A and FIG. 3B, a buffer sample inlet stream 55 of pH 9 flows toward the detection channel T-joint 58 from the right inlet channel 50. The buffered solution (pH 9) appears as a dark (clear) fluid. A weakly buffered indicator dye (Carboxy-SNAFL 1) inlet stream 45 of pH 5.5 entered from the left in indicator stream inlet channel 40. The dynamic range of Carboxy-SNAFL 1 is from pH 6.5 to pH 8.5. In its acid form the dye fluoresces as yellow (shown as light gray area 130) whereas in the base form the dye fluoresces as a deep red (shown as dark gray area 140). The pH 5.5 indicator stream is well outside the dynamic range of the indicator dye in its acid form. Conversely, the sample stream is well outside the dynamic range of the indicator dye in its base form.

A rapid transition from the acid form of the indicator dye to the base form of the dye forms an isoconcentration curve 130 shown in FIG. 3. This "compression" of the dynamic range of the indicator dye is a result of dye signal saturation beyond both extremes of its dynamic range. For maximum sensitivity the indicator dye stream pH should be adjusted to a pH near the edge of the dynamic range of the dye. The extreme values of pH used in this experiment were selected to dramatically illustrate the correlation between flow rate, analyte concentration, dye concentration, analyte diffusivity, dye diffusivity, and the "resting location" of the compressed dynamic range transition zone "line."

Figure 4:
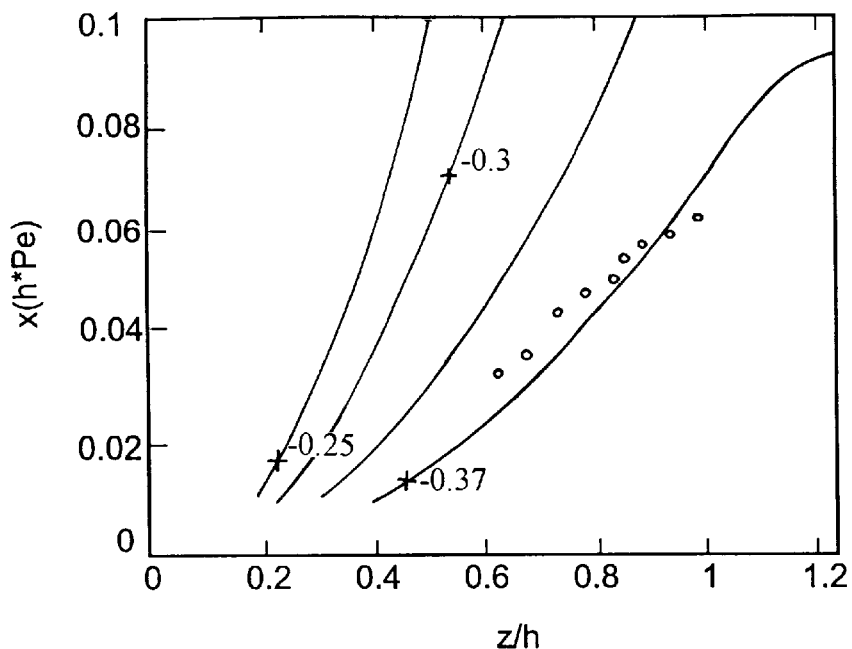
FIG. 4 shows concentration contours generated by the method of this invention for hydrogen ion concentration using unbuffered sample and indicator streams.

FIG. 4 is a graph showing the nondimensional isoconcentration curves generated as a calibration model for hydroxide ion concentration as described in Example 3 below for an unbuffered sample stream using nine observed measurements and indicated by small circles in FIG. 4. The numbers next to each isoconcentration curve represent the nondimensional concentration $\gamma$ of the substance whose concentration is being measured along that curve. Each nondimensional isoconcentration curve corresponds to the actual isoconcentration curve which would be observed in the same system from which these curves were generated using a particular initial sample concentration $c_0$. The initial sample concentration for a sample of unknown concentration may be determined using the calibration model of FIG. 4 by:

(1) introducing the sample stream into a system identical or substantially identical to that used to calculate the nondimensional isoconcentration curves;

(2) observing the location (z and x coordinates) of a point or points on the isoconcentration curve formed in the indicator stream which will have a known concentration c at such point or points;

(3) nondimensionalizing the location of these observed points by dividing the horizontal coordinate z by h, the half-channel depth, and dividing the vertical coordinate x by h times the Peclet number of the indicator stream $Pe_1$;

(4) determining the nondimensional isoconcentration curve of FIG. 4 to which these nondimensionalized observed points correspond, and reading the nondimensional concentration $\gamma$ corresponding to these points from the graph of FIG. 4 or data tables for the data graphed in FIG. 4;

(5) calculating the initial concentration of the sample stream $c_0$ using the formula:

$$c_0 = (c - c_{eq})/\gamma$$

The quantity $c_{eq}$ is calculated at the time the nondimensional isoconcentration curves are generated.

Figure 5:
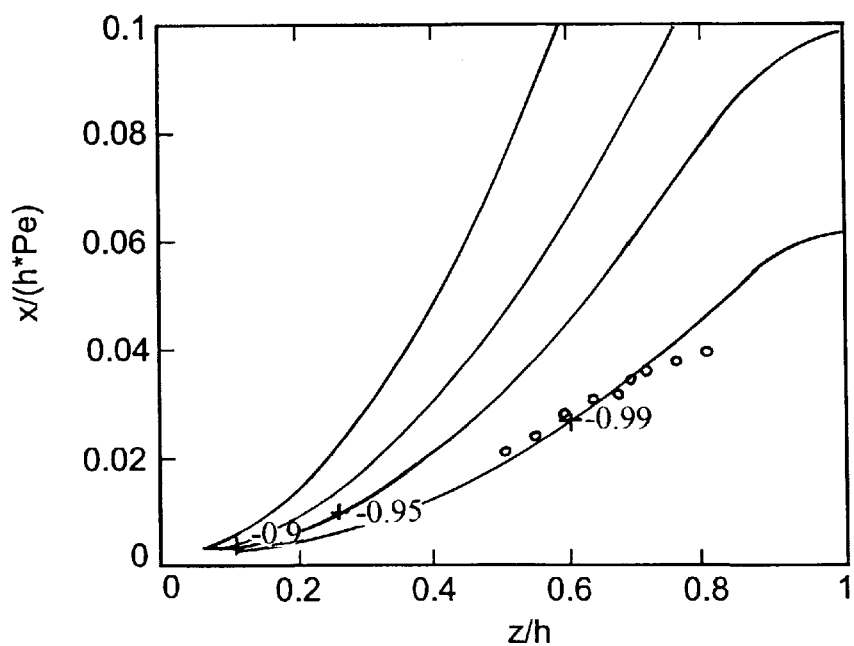
FIG. 5 shows concentration contours generated by the method of this invention for hydrogen ion concentration using highly buffered sample and an unbuffered indicator stream.

FIG. 5 is a graph showing the nondimensional isoconcentration curves generated in Example 3 below for a system similar to that of FIG. 4 but using a fully buffered sample stream. Nine observed measurements were taken from the observed isoconcentration curve, indicated by small circles in FIG. 5. In the ideally buffered system, the equilibrium concentration $c_{eq}$ is the same as the initial concentration $c_0$.

Figure 6:
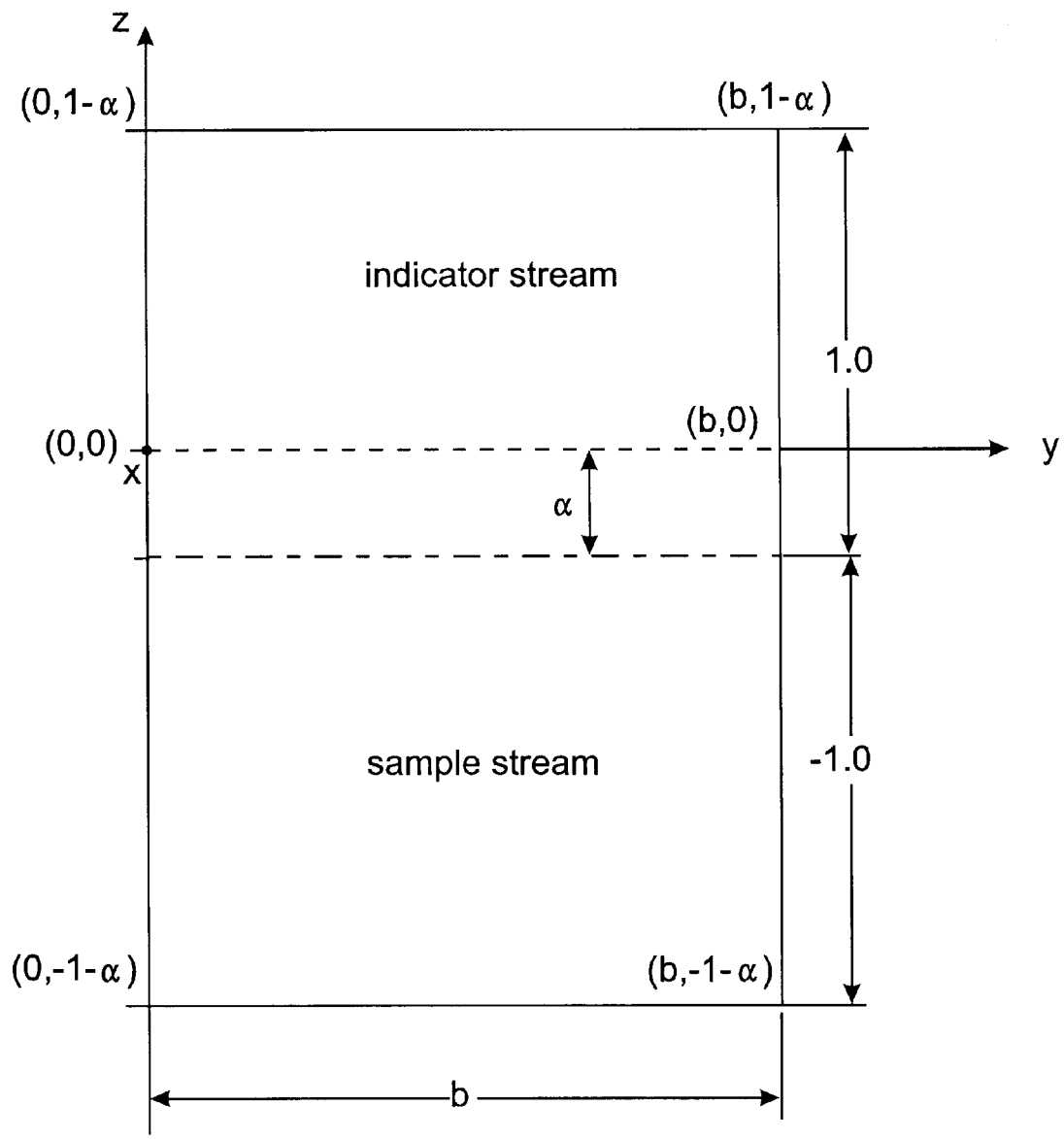
FIG. 6 is a diagram used to illustrate the rectangular duct cross-section for the two-viscosity velocity problem.

FIG. 6 is a diagram used to illustrate the rectangular duct cross-section.

Figure 7:
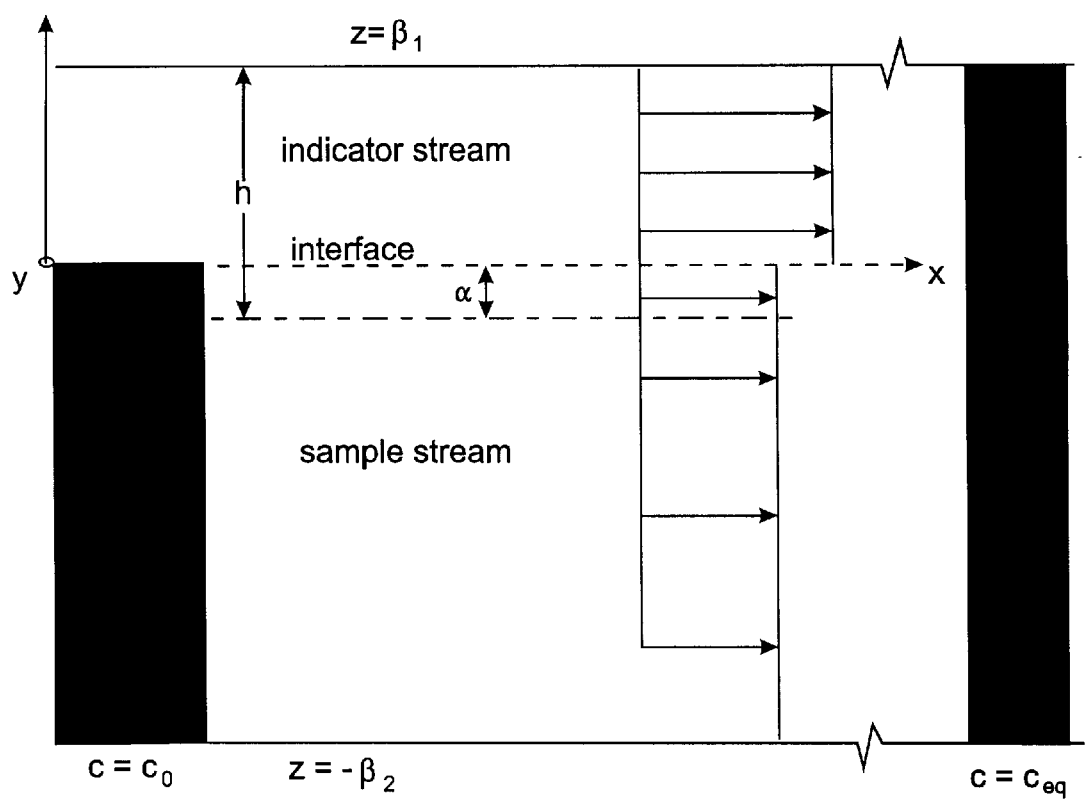
FIG. 7 is a diagram used to illustrate the two-Peclet diffusion problem, where the average velocity of each stream replaces the velocity distribution.

FIG. 7 is a diagram used to illustrate the geometric parameters used in the two-Peclet diffusion problem. The z axis, shown vertically, is the horizontal axis of FIGS. 1 and 3. The dark region at the lower left marked $c=c_0$ indicates the concentration of the entering sample stream. The dark region at the right marked $c=c_{eq}$ indicates the equilibrium concentration when the concentration in the sample stream is equal to the concentration in the indicator stream.

The general problem of estimating the concentration of a single analyte present in the sample stream from an absorbance or fluorescence signal which is sampled at various positions in the T-sensor detection channel requires: 1) a means of estimating the local concentration of the analyte, and 2) a means of relating this concentration to the concentration present in the sample stream. For example, if an RGB detector is used, the local analyte concentration is given in symbolic functional form as $$c(x,z)=c(I_{red}(x,z), I_{blue}(x,z), I_{green}(x,z), c_{dye}(x,z); I_{excitation}, w) \quad (1)$$

where: $I_{red}$ is the red intensity, $I_{blue}$ is the blue intensity, $I_{green}$ is the green intensity, $c_{dye}$ is the indicator dye concentration, $I_{excitation}$ is the excitation light intensity, and w is the optical path length of the detection channel.

The analyte concentration determination procedure of this invention may be summarized as:

1. Select detection points (x,z) within the detection channel;
2. Measure the fluorescence or absorbance signal at points (x,z) in either RGB (red, blue, green) or grayscale intensity;
3. Use the equations provided herein to calculate the concentration of dye $c_{dye}$ at points (x,z);
4. Use the calibration response surface represented symbolically by Eq. 1 to estimate the concentration of the analyte of interest at points (x,z) c(x,z);
5. Use the equations provided herein to calculate the concentration of analyte $c_0$ present in the sample stream before it enters the device.

A preferred method of this invention comprises calculating as an analytical model a graph or data representing at least one, and preferably about 10–40 nondimensional isoconcentration curves corresponding to the nondimensionalized isoconcentration curves that would be observed using different initial concentrations of analyte particles in the sample stream.

To calculate the analytical model, a device providing laminar flow of sample and indicator streams in a flow channel having rectangular or near rectangular dimensions is hypothesized, for example, a T-sensor device. The actual flow channel may be etched by conventional anisotropic etching techniques along the {100} plane of a silicon microchip, in which case the channel will have slanted sides and actually be trapezoidal. However, when the angled sides are short compared to the other dimensions, this deviation from the rectangular may be ignored for purposes of calculation. The channel may also be etched by means which directly produce rectangular grooves such as reactive ion etching (RIE). The junction of inlet streams may comprise other similar geometries such as the T-junction being replaced by a Y-junction.

A sample stream comprising diffusible analyte particles is introduced into the flow channel along with an indicator stream comprising an indicator substance capable of making an observable change when analyte particles are present at a known concentration.

The axial coordinate x along the flow channel is measured from the input end of the channel. The horizontal coordinate z is measured from the interface between the sample and indicator streams at x=0. The origin of the coordinates x and z is shown in FIG. 1 as 0. In FIG. 1, the sample stream and indicator stream have equal flow rates and viscosities and the interface between the two streams is at the midline of the flow channel. However, in general the sample and indicator flow rates and the viscosity of each stream are different, and the interface between the two streams may be offset from the midline. The information needed as input to calculate the analytical model is:

$q_2/q_1$ Where $q_1$ is the flow rate of the indicator stream and $q_2$ is the flow rate of the sample stream. Flow rates may be controlled at input or measured by means known to the art.

$D_2/D_1$ Where $D_1$ is diffusivity of the analyte particles in the indicator stream and $D_2$ is diffusivity of the analyte particles in the sample stream. This may be determined by reference to published tables.

h Half the channel dimension in the diffusion direction.

α Interface offset from the centerline normalized by h (half the channel depth). This may be determined by measuring the distance from the channel midline to the point of observable change of the indicator substance at the point where the two streams first come together.

c The concentration of analyte particles in the indicator stream at the points of observable change of the indicator substance. For example, a pH indicator may change colors at a known hydrogen ion concentration. Other indicator substances may fluoresce or otherwise react in the presence of a known concentration of analyte particles.

As an alternative to determining α the interface location by observation, if the viscosity ratio, $\mu_2/\mu_1$, the ratio of sample to indicator stream viscosity is known, α can be calculated from the viscosity ratio.

As set forth above for any given interface location, either observed at the upstream end of the flow channel where the isoconcentration line begins, or arbitrarily assigned, the viscosities can be calculated.

From the foregoing input information, a model can be calculated which provides the initial concentration $c_0$ of analyte particles in a test sample stream corresponding to an observable change in the indicator substance at any z and x coordinate in the indicator stream.

The test system in which the initial concentration of a sample stream is determined using the calibration model must be substantially similar to the system used to generate the model, whether actual or hypothetical, i.e., the test device must have the same dimensions and use the same type of indicator stream, the flow rate ratio must be the same, and the viscosity ratio of the sample to indicator stream must be the same for both the test system and the system used to generate the model. To use the model to test for an unknown initial sample stream concentration, it is only necessary to measure z and x coordinates of a point or points (preferably about 9 or 10 points) on an isoconcentration line in the indicator stream, e.g. where there is a color change indicating that a known concentration of analyte particles has diffused from the sample stream and is present at these points. From this it may be determined from the previously calculated model what the initial concentration of the sample stream must be to give an observable change at these points.

In a preferred embodiment where the interface location α is known even if the viscosities $\mu_1$ and $\mu_2$ of the two streams are not known, the average velocity of each stream, $U_1$ and $U_2$ may be calculated and used to calculate the Peclet numbers, $Pe_1$ and Pe2, for each stream, to derive an expression for the nondimensional concentration of analyte particles at any given point in the indicator stream as described below.

In the case where the viscosities of the two streams are known, it is not necessary to know the location of the interface between the streams. In the case where the viscosities of the two streams are known, the average velocity of each stream $U_1$ and $U_2$ and the location of the interface between the streams α is calculated as described below.

When the average stream velocities $U_1$ and $U_2$ are known and used to calculate the Peclet numbers for each stream $Pe_1$ and $Pe_2$, the partial differential equation $$\frac{\partial^2 \gamma}{\partial \tilde{z}^2} = \frac{Pe \partial \gamma}{\partial \tilde{x}} \qquad (2)$$

is solved as described below, so that n isoconcentration lines along which $\gamma$ is a constant $\gamma_n$, such as those shown in FIG. 4, may be graphed or stored in tabular form.

Provided herein is a method for generating a calibration model comprising data representative of a series of nondimensional isoconcentration lines, useful to determine the initial concentration of diffusible particles in a test sample stream comprising said particles and a sample carrier liquid, introduced into a rectangular flow channel having a known width, and a known depth, and having two sidewalls, a top wall and a bottom wall, and sized to permit laminar flow of two streams therein, said test sample stream being in laminar flow with a test indicator stream comprising an indicator substance capable of exhibiting a detectable change in contact with a known concentration of said particles and an indicator carrier liquid introduced into said flow channel, whereby the indicator substance exhibits its detectable change along an observable isoconcentration line in said indicator stream.

The method for generating the reference data comprises:
(a) providing input information including:
  (1) $(q_2/q_1)$, the ratio of the flow rate of a sample stream, namely $q_2$, to the flow rate of an indicator stream, namely $q_1$;
  (2) $D_2/D_1$, the ratio of the diffusivity of the diffusible particles in the sample stream, namely $D_2$, to the diffusivity of the diffusible particles in the indicator stream, namely $D_1$;
  (3) h, half the channel depth, which defines an axial midline for said channel;
  (4) $\alpha$, the distance of the interface between said sample and indicator streams, at the furthest upstream point on said observable isoconcentration line, from said midline, divided by h; or alternatively, the ratio of the viscosity of the sample stream, namely $\mu_2$, to the viscosity of the indicator stream, namely $\mu_1$;
(b) using said flow rate ratio to calculate the average velocity, namely $U_1$, of the indicator stream, and the average velocity, namely $U_2$, of the sample stream, and calculating the ratio of the average velocity of the sample stream to the average velocity of the indicator stream, namely $U_2/U_1$;
(c) when $\alpha$ has been provided, calculating the ratio of the viscosity of the sample stream to the viscosity of the indicator stream, namely $\mu_2/\mu_1$; or alternatively, when the viscosity data has been provided in step (4) rather than $\alpha$, calculating $\alpha$ (the distance of the interface between said sample and indicator streams, at the furthest upstream point on an observable isoconcentration line, from said midline, divided by h);
(d) calculating an expression for the equilibrium concentration, namely $c_{eq}$, of said particles in said channel, namely $$c_{eq} = \frac{c_0}{1 + \frac{U_1 \beta_1}{U_2 \beta_2}}; \qquad (3)$$

(e) defining $\gamma$, the nondimensional concentration, as $$\gamma = (c - c_{eq})/c_0; \qquad (4)$$

(f) calculating $Pe_1$, the Peclet number of the indicator stream;
(g) calculating a set of data representative of a plurality of n nondimensionalized isoconcentration lines along which $\gamma = \gamma_n$ is constant and corresponding to the location of isoconcentration lines which would be observable when samples of differing specific initial concentrations of said particles were introduced into said system, the location of said isoconcentration lines being nondimensionalized by dividing the x coordinate of each point on an observable isoconcentration line by h times the Peclet number of the indicator stream ($Pe_1$), and by dividing the z coordinate by h, as shown in FIG. 4.

The calculations described above are applicable to determining the concentrations of analyte particles at different locations in an indicator stream, and include the case described in below where the concentration is the hydroxide ion concentration in an unbuffered system. If the system is buffered so that the pH of the sample stream does not change, the calculations to determine the nondimensional concentrations $\gamma_n$ are simplified as described below.

For either the unbuffered or buffered sample stream case, the isoconcentration lines, i.e. the values for $\gamma_n$ calculated as described above, it is possible to determine the initial concentration $c_0$ of the sample stream from the relationship $$\gamma_n = (c_n - c_{eq})/c_0 \qquad (5)$$

where $\gamma_n$ is the nondimensional concentration at any point along an isoconcentration line, $c_n$ is the actual concentration at any point $\tilde{x}, \tilde{z}$ known by an observed change in the indicator substance at the corresponding point $\tilde{x}, \tilde{z}$, and $c_{eq}$ is the equilibrium concentration in the system (Eq. 5).

In practice, in using the method of this invention to determine the initial concentration of an unknown sample, the various quantities set forth above are determined, and the calculations made as set forth below, then for comparing the observed isoconcentration curve with the model to find a nondimensional isoconcentration curve to which it most nearly corresponds, it is preferred that the observed isoconcentration curve be nondimensionalized by dividing the x coordinates by the quantity $h \cdot Pe_1$ and the z coordinate by h as shown in FIG. 1. The analytical model can then be used to determine what initial sample concentration the observed, nondimensionalized coordinates correspond to.

In a preferred embodiment the sample stream is a physiological fluid such as whole blood, plasma, urine or cerebrospinal fluid, and the diffusible particles are selected from the group consisting of electrolytes, proteins, enzymes, drugs, hormones, toxins, bacteria, viruses and diffusible cells.

Calibration Model

Diffusion in one cross-stream direction only and convection along the channel only for a steady, non-reacting system are considered. The species conservation equation (Cussler, E. L., *Diffusion, Mass Transfer in Fluid Systems*, Clarendon Press, Oxford, 1984) is represented by the following partial differential equation when is it assumed no variations exist in the y-direction and diffusion in the x-direction is negligible:

$$\frac{D \partial^2 c(x,z)}{\partial z^2} = u(z)\frac{\partial c(x,z)}{\partial x}, \quad (6)$$

An analytical solution for the velocity distribution u(y,z) for equal, constant viscosity streams in a duct of rectangular cross-section is known (Shah, R. K. and London, A. L., *Laminar Flow Forced Convection in Ducts*, Academic Press, New York, 1978). However, the method of this invention utilizes a mathematical solution not previously available to calculate the velocity profile u(y,z) in the case of two streams of different viscosity and volume flow rate.

If the sample and indicator streams have different viscosities, the average velocity $U_i$ is generally different for each stream. The foregoing equation in that case based on the average velocity in each stream is given by $$\frac{D_i \partial^2 c_i}{\partial z^2} = \frac{U_i \partial c_i}{\partial x}, \quad (7)$$

where i=1 refers to the indicator stream and i=2 the sample stream. The above equation is justified for arbitrary aspect ratios for the case of interest because the boundary condition at z=0 is that the concentration at the inlet to the flow channel is uniform in the y-direction but substantially non-uniform in the z-direction. Thus, diffusion in the y-direction can be ignored compared to diffusion in the z-direction.

Nondimensionalized with $$\tilde{z} = \frac{z}{h}, \tilde{x} = \frac{x}{h}, \gamma = \frac{(c - c_{eq})}{c_0}, \quad (8)$$

the foregoing partial differential equations become $$\frac{\partial^2 \gamma_i}{\partial \tilde{z}^2} = \frac{Pe_i \partial \gamma_i}{\partial \tilde{x}}, \quad (9)$$

where $Pe_i = U_i h/D_i$ is the Peclet number in each stream and denotes the relative magnitude of mass transfer by convection to mass transfer by diffusion.

Rectangular Duct Two-viscosity Velocity Distribution

FIG. 6 diagrams the problem to be solved in calculating the average velocity in each stream and the interface location in a system where the viscosities of both the sample and indicator streams are known. The dimensions have all been nondimensionalized by h (half the z-direction [diffusion direction] dimension). The defining partial differential equations (P.D.E.'s) are $$\frac{\partial^2 u_1}{\partial z^2} = \frac{\partial^2 u_1}{\partial y^2} = \left(\frac{1}{\mu_1}\right)\left(\frac{dP}{dx}\right) \quad (10)$$

and $$\frac{\partial^2 u_2}{\partial z^2} = \frac{\partial^2 u_2}{\partial y^2} = m12\left(\frac{1}{\mu_1}\right)\left(\frac{dP}{dx}\right), \quad (11)$$

where m12 is the viscosity ratio $\mu_1/\mu_2$. Nondimensionalizing y and z by h, the velocities $u_1$ and $u_2$ yield $$y^* = \frac{y}{h}, z^* = \frac{z}{h} \text{ and } u_i^* = \frac{u_i}{\left(\frac{1}{\mu_1}\right)\left(\frac{dP}{dx}\right) \cdot h^2}. \quad (12)$$

The resulting nondimensional form of the P.D.E.'s is given by $$\frac{\partial^2 u_1}{\partial z^2} = \frac{\partial^2 u_1}{\partial y^2} = 1 \quad (13)$$

$$\frac{\partial^2 u_1}{\partial z^2} = \frac{\partial^2 u_2}{\partial y^2} = m12 \quad (14)$$

where the * notation has been dropped.

The boundary conditions (B.C.'s) that apply are the no slip condition at the walls, the symmetry condition on the centerline (y=0) and matched velocity and shear stress at the interface.

$$u_1(y, 1-\alpha)=0 \; u_2(y,-1-\alpha)=0 \; u_1(b,z) =0 \; u_2(b,z)=0 \quad (15)$$

$$\frac{\partial u_1}{\partial y}(0, z) = 0 \quad \frac{\partial u_2}{\partial y}(0, z) = 0 \quad \text{symmetry} \quad (16)$$

$$u_1(y, 0) = u_2(y, 0) \quad \frac{\partial u_1}{\partial z}(y, 0) = m12\frac{\partial u_2}{\partial z}(y, 0) \quad (17)$$

matched interface

The problem can be turned into a homogenous problem by using a variable transformation consistent with 1. The P.D.E.'s become homogenous.
2. The transformed velocities go to zero at the walls perpendicular to the z-axis. This will eliminate Gibb's phenomena in the z-direction.
3. The transformed velocities $v_1$ and $v_2$ match at the interface. This will eliminate Gibb's phenomena at the interface.
4. The derivatives of the transformed velocities are directly proportional at the interface. A transformation that satisfies the above conditions is given by $$u_1(y, z) = v_1(y, z) + \frac{z^2}{2} + A_1 z + B \quad (18)$$

$$u_2(y, z) = v_2(y, z) + \frac{m12 \cdot z^2}{2} + m12 \cdot A_1 \cdot z + B. \quad (19)$$

By substitution of the transformed variables into the P.D.E.'s and B.C.'s, the following transformed P.D.E.'s and B.C.'s are developed.

$$\frac{\partial^2 v_1}{\partial z^2} + \frac{\partial^2 v_1}{\partial y^2} = 0 \quad \frac{\partial^2 v_2}{\partial z^2} + \frac{\partial^2 v_2}{\partial y^2} = 0. \quad (20)$$

The P.D.E.'s are homogenous as required.

$$v_1(y,1-\alpha)=0 \; v_2(y,-1-\alpha)=0. \quad (21)$$

The velocity is zero at the walls perpendicular to z axis as required.

$$\frac{\partial v_1}{\partial y}(0, z) = \frac{\partial v_2}{\partial y}(0, z) = 0. \tag{22}$$

The symmetry conditions yield $$v_1(y, 0) = v_2(y, 0) \quad \frac{\partial v_1}{\partial z}(y, 0) = m21 \frac{\partial v_2}{\partial z}(y, 0), \tag{23}$$

where m12 is $\mu_1/\mu_2$ and m21 is $\mu_2/\mu_1$.
The interface matching boundary condition becomes $$v_1(b, z) = \frac{z^2}{2} - A_1 z - B \tag{24}$$

$$v_2(b, z) = \frac{m12 \cdot z^2}{2} - m12 \cdot A_1 \cdot z - B,$$

where $$A_1 = \frac{m12(1 + 2\alpha + \alpha^2) - 1 + 2\alpha - \alpha^2}{2(1 - \alpha + m12 + \alpha m12)} \tag{25}$$

and $$B = \frac{2 \cdot m12 \cdot (\alpha^2 - 1)}{2(1 - \alpha + m12 + \alpha \cdot m12)}. \tag{26}$$

The transformed boundary value problem can now be solved by separation of variables. For each stream $$\frac{\partial^2 v_i}{\partial z^2} + \frac{\partial^2 v_i}{\partial y^2} = 0 \tag{27}$$

where $i=1, 2$ denotes the indicator and sample streams, respectively.
Choosing $$v_i(y,z)1 = Z_i(z) Y_i(y) \tag{28}$$

yields $\dfrac{Y_i''}{Y_i} = \dfrac{Z_i''}{Z_i} = -\lambda^2$. \hfill (29)

The solution is given by $$v_1(y,z) = [D_1 \cos h(\lambda_1 y) + E_1 \sin h(\lambda_1 y)] \cdot [B_1 \cos (\lambda_1 z) + C_1 \sin (\lambda_1 z)] \tag{30}$$

and $$v_2(y,z) = [D_2 \cos h(\lambda_2 y) + E_2 \sin h(\lambda_2 y)] \cdot [B_2 \cos (\lambda_2 z) + C_2 \sin (\lambda_2 z)] \tag{31}$$

where A, B, C, D, E and G are arbitrary constants.
Applying the symmetry conditions eliminates $E_1$ and $E_2$.
The boundary conditions $$v_1(y, 1-\alpha) = 0 \quad v_2(y, -1-\alpha) = 0 \tag{32}$$

and the identities $$\sin(\alpha-\beta) = \sin\alpha\cos\beta - \cos\alpha\sin\beta \quad \sin(\alpha+\beta) = \sin\alpha\cos\beta + \cos\alpha\sin\beta \tag{33}$$

reduce the solution to $$v_1(y,z) = G_1 \cos h(\lambda_1 y) \sin[\lambda_1(1-\alpha-z)] \tag{34}$$

$$v_2(y,z) = G_2 \cos h(\lambda_2 y) \sin[\lambda_2(1+\alpha+z)]. \tag{35}$$

The interface boundary conditions yield the characteristic equation $$\sin[\lambda_n(1+\alpha)]\cos[\lambda_n(1-\alpha)] + m21 \cdot \sin[\lambda_n(1-\alpha)]\cos[\lambda_n(1+\alpha)] = 0 \tag{36}$$

The roots $\lambda_n$ of this characteristic equation are the eigenvalues of the problem.

In terms of the infinite set of eigenvalues, the solution can be written as $$v_1(y, z) = \sum_{n=1}^{\infty} G_{1n} \cosh(\lambda_n y) \sin[\lambda_{1n}(1 - \alpha - z)] \tag{37}$$

$$v_2(y, z) = \sum_{n=1}^{\infty} G_{1n} \frac{\sin[\lambda_{1n}(1 - \alpha)]}{\sin[\lambda_{1n}(1 + \alpha)]} \cosh(\lambda_{1n} y) \sin[\lambda_{1n}(1 + \alpha + z)] \tag{38}$$

The constants $G_{1n}$ can be found by applying the last boundary conditions. First simplify by letting $$H_n = G_{1n} \sin[\lambda_{1n}(1-\alpha)] \tag{39}$$

and $$I_n = H_n \cos h(\lambda_{1n} b). \tag{40}$$

The B.C at $y=b$ yields $$-\frac{z^2}{2} - A_1 z - B = \sum_{n=1}^{\infty} \frac{\sin[\lambda_{1n}(1 - \alpha - z)]}{\sin[\lambda_{1n}(1 - \alpha)]} = \sum_{n=1}^{\infty} I_n Z_{1n}(z), \tag{41}$$

$$0 < z < 1 - \alpha$$

$$-m12 \frac{z^2}{2} - m12 \cdot A_1 \cdot z - B = \sum_{n=1}^{\infty} I_n \frac{\sin[\lambda_{1n}(1 + \alpha + z)]}{\sin[\lambda_{1n}(1 + \alpha)]} = \sum_{n=1}^{\infty} I_{1n} Z_{2n}(z), \tag{42}$$

$$-1 - \alpha < z < 0$$

where the $Z_n$'s are the eigenfunctions.
The $I_n$'s can be found from the theory of orthogonal functions, such that $$\int_{-1-\alpha}^{1-\alpha} P \cdot Z_n \cdot Z_m dz = 0 \tag{43}$$

where P is a weighting function that can be found by substituting the eigenfunctions into the Z(z) differential equation and applying the orthogonality condition $$\int_{-1-\alpha}^{0} P_2 [Z_{2m}' Z_{2n} - Z_{2n}' Z_{2m}]' dz + \int_{0}^{1-\alpha} P_1 [Z_{1m}' Z_{1n} - Z_{1n}' Z_{1m}]' dz = 0, \tag{44}$$

whose primes denote derivatives with respect to Z.

$$P_2 [Z_{2m}' Z_{2n} - Z_{2n}' Z_{2m}]_{-1-\alpha}^{0} + P_1 [Z_{1m}' Z_{1n} - Z_{1n}' Z_{1m}]_{0}^{1-\alpha} = 0 \tag{45}$$

The interface matching conditions given by Equation (25) yield $$P_1 Z_{1n}'(0^+) = P_2 Z_{2n}'(0^-) \tag{46}$$

$$\therefore P_1 = 1, P_2 = m21 \tag{47}$$

The coefficients $I_n$ can be calculated from the properties of orthogonal functions with P known, $$I_n = \frac{\int_{-1-\alpha}^{1-\alpha} P \cdot Z_n \cdot v(b, z) \cdot dz}{\int_{-1-\alpha}^{1-\alpha} P \cdot Z_n^2 \cdot dz} \tag{48}$$

These integrals were evaluated using Maple mathematics software package (Waterloo Maple, Inc.). The following relations resulted.

$$I_n = \frac{I3 + I4}{I1 + I2}, \tag{49}$$

$$I1 = \frac{m21}{\sin^2[\lambda_{1n}(1-\alpha)]}\left\{\frac{\lambda_{1n}(1+\alpha) - \sin[\lambda_{1n}(1+\alpha)]\cos[\lambda_{1n}(1+\alpha)]}{2\lambda_{1n}}\right\}, \tag{50}$$

$$I2 = \frac{1}{\sin^2[\lambda_{1n}(1+\alpha)]}\left\{\frac{\lambda_{1n}(1-\alpha) - \sin[\lambda_{1n}(1-\alpha)]\cos[\lambda_{1n}(1-\alpha)]}{2\lambda_{1n}}\right\}, \tag{51}$$

$$I3 = \frac{-1}{\sin[\lambda_{1n}(1+\alpha)]}\{SI13 + SI23 + SI33\}, \tag{52}$$

$$SI13 = \frac{1}{2\lambda_{1n}^3}\{2\cos[\lambda_{1n}(1+\alpha)] + \lambda_{1n}^2(1+\alpha)^2 - 2\}, \tag{53}$$

$$SI23 = A_1\left\{\frac{\sin[\lambda_{1n}(1+\alpha]}{\lambda_{1n}^2} - \frac{(1+\alpha)}{\lambda_{1n}}\right\}, \tag{54}$$

$$SI33 = \frac{B \cdot m21}{\lambda_{1n}}\{1 - \cos[\lambda_{1n}(1+\alpha)]\}, \tag{55}$$

$$I4 = \frac{-1}{\sin[\lambda_{1n}(1-\alpha)]}\{SI14 + SI24 + SI34\}, \tag{56}$$

$$SI14 = \frac{1}{2\lambda_{1n}^3}\{2\cos[\lambda_{1n}(1-\alpha)] + \lambda_{1n}^2(1-\alpha)^2 - 2\}, \tag{57}$$

$$SI24 = A_1\left[\frac{(1-\alpha)}{\lambda_{1n}} - \frac{\sin[\lambda_{1n}(1-\alpha)]}{\lambda_{1n}^2}\right], \tag{58}$$

and $$SI34 = \frac{B}{\lambda_{1n}}\{1 - \cos[\lambda_{1n}(1-\alpha)]\}. \tag{59}$$

The untransformed velocities are retrieved using Equations (18) and (19).

The final result for the velocity profile in the flow channel is $$u_1(z, y) = \sum_{n=1}^{\infty} I_n \frac{\sin[\lambda_n(1-\alpha-z)]}{\sin[\lambda_n(1-\alpha)]}\left[\frac{\cosh(\lambda_n y)}{\cosh(\lambda_n b)} - 1\right] \tag{60}$$

and $$u_2(z, y) = \sum_{n=1}^{\infty} I_n \frac{\sin[\lambda_n(1+\alpha-z)]}{\sin[\lambda_n(1+\alpha)]}\left[\frac{\cosh(\lambda_n y)}{\cosh(\lambda_n b)} - 1\right]. \tag{61}$$

FIG. 2 graphs these equations for a typical set of parameters. With these expressions the diffusion problem can now be solved.

Calculation of Nondimensional Concentrations

FIG. 7 is a diagram showing the region of the device in which the nondimensional concentration $\gamma(x,z)$ is calculated by solving the equations:

$$\frac{\partial^2 \gamma_1}{\partial z^2} = Pe_1 \frac{\partial \gamma_1}{\partial x} \tag{62}$$

-continued $$\frac{\partial^2 \gamma_2}{\partial z^2} = Pe_2 \frac{\partial \gamma_2}{\partial x}, \tag{63}$$

where 1 denotes the indicator stream, and 2 denotes the sample stream.

For the general case of different Pe in each stream, the following boundary conditions (BC's) apply:

$\gamma_1(\infty, \tilde{z})=0$ $\gamma_2(\infty, \tilde{z})=0$ (exiting equilibrium condition).

These boundary conditions express the assumption that when the concentration of analyte particles in the sample and indicator streams reaches equilibrium ($c_{eq}$), at an infinite axial distance ($\tilde{x}$) along the channel, the concentration c at any point across the channel is $c_{eq}$, and therefore the nondimensional concentration $\gamma_i$ is 0.

$$\frac{\partial \gamma_1(x, \beta_1)}{\partial z} = \frac{\partial \gamma_2(x, -\beta_2)}{\partial z} = 0 \quad \text{(no wall flux)}. \tag{64}$$

This expresses the assumption that the analyte does not pass through the channel walls.

$\gamma_1(x, 0)=\gamma_2(x, 0)$ (concentration match). (65)

This expresses the assumption that the concentrations on either side of the interface in the sample stream and the indicator stream at any given point along the length of the channel are the same.

$$D_1 \frac{\partial \gamma_1(x, 0)}{\partial z} = D_2 \frac{\partial \gamma_2(x, 0)}{\partial z} = 0 \quad \text{(flux match)}. \tag{66}$$

This expresses the assumption that the flux of particles leaving one stream at the interface is the same as the flux of particles entering the other stream at the interface. Since $D_1$ does not necessarily equal $D_2$ the derivatives do not match at the interface, just the fluxes.

$\gamma_1(0, z)=-\Gamma$, $\gamma_2(0, z)=1-\Gamma$, (entering conditions) (67)

Note the actual concentrations are not functions of y at x=0, and therefore justify ignoring diffusion in that direction.

By applying separation of variables the general solution in each stream can be written $$\gamma_1(x, z) = \exp\left\{\frac{-\lambda_1^2}{Pe_1}x\right\}[A_1\cos(\lambda_1 z) + B_1\sin(\lambda_1 z)], \tag{68}$$

and $$\gamma_2(x, z) = \exp\left\{\frac{-\lambda_2^2}{Pe_2}x\right\}[A_2\cos(\lambda_2 z) + B_2\sin(\lambda_2 z)]. \tag{69}$$

The exiting boundary condition has been applied which yields the negative exponential. The no-flux boundary condition in the indicator stream and the identity $\cos \alpha \cos \beta + \sin \alpha \sin \beta = \cos(\alpha-\beta)$ (70)

yield $$\gamma_1(x, z) = A_1 \exp\left\{\frac{-\lambda_1^2 x}{Pe_1}\right\} \cos[\lambda_1(\beta_1 - z)] \tag{71}$$

Similarly, the no-flux boundary condition in the sample stream and the identity $$\cos\alpha \cos\beta - \sin\alpha \sin\beta = \cos(\alpha+\beta) \tag{72}$$

yield $$\gamma_2(x, z) = A_2 \exp\left\{\frac{-\lambda_2^2 x}{Pe_2}\right\} \cos[\lambda_2(\beta_2 + z)] \tag{73}$$

For the first interface matching boundary condition to hold for all x $$A_1 \exp\left\{\frac{-\lambda_1^2 x}{Pe_1}\right\} \cos[\lambda_1(\beta_1 - z)] = A_2 \exp\left\{\frac{-\lambda_2^2 x}{Pe_2}\right\} \cos[\lambda_2(\beta_2 + z)], \tag{74}$$

$$\frac{\lambda_1^2}{Pe_1} = \frac{\lambda_2^2}{Pe_2}, \tag{75}$$

or with the definition $$k = \sqrt{\frac{Pe_2}{Pe_1}} \tag{76}$$

$$\lambda_2^2 = k^2 \lambda_1^2, \quad \lambda_2 = k\lambda_1. \tag{77}$$

With the definitions $$A_1 = C \cos(k\lambda_1 \beta_2), \quad A_2 = C \cos(\lambda_1 \beta_1) \tag{78}$$

the resulting equation for concentration in each region becomes $$\gamma_1(x, z) = C \cos(k\lambda_1 \beta_2) \cos[\lambda_1(\beta_1 - z)] \exp\left\{-\frac{\lambda_1^2 x}{Pe_1}\right\}, \tag{79}$$

and $$\gamma_2(x, z) = C \cos(\lambda_1 \beta_1) \cos[k\lambda_1(\beta_2 + z)] \exp\left\{-\frac{k^2 \lambda_1^2 x}{Pe_2}\right\}. \tag{80}$$

The second interface matching boundary condition is, $$D_1 \cos(k\lambda_1\beta_2) \sin(\lambda_1\beta_1) = -D_2 k \cos(\lambda_1\beta_1) \sin(k\lambda_1\beta_1) \tag{81}$$

which yields the characteristic equation $$\cos(k \cdot \lambda_{1n}\beta_2) \cdot \sin(\lambda_{1n}\beta_1) + \frac{D_2}{D_1} k \cdot \cos(\lambda_{1n}\beta_1) \cdot \sin(k\lambda_{1n}\beta_2) = 0. \tag{82}$$

With $$\sigma = \frac{D_2}{D_1} k \tag{83}$$

the above equation becomes $$\cos(k \cdot \lambda_{1n}\beta_2) \cdot \sin(\lambda_{1n}\beta_1) + \sigma \cdot \cos(\lambda_{1n}\beta_1) \cdot \sin(k\lambda_{1n}\beta_2) = 0 \tag{84}$$

The eigenvalues ($\lambda_{1n}$'s) are the roots of this characteristic equation.

The eigenfunctions are $$\Phi_n(z) = \cos(k\lambda_{1n}\beta_2) \cos[\lambda_{1n}(\beta_1-z)], \quad 0 > z > \beta_1 = \cos(\lambda_{1n}\beta_1) \cos[k\lambda_{1n}(\beta_2+z)], \quad -\beta_2 > z > 0 \tag{85}$$

Note: $\lambda_{1n}$ is replaced by $\lambda_n$ in the following equations. The orthogonality condition including the weighing function P is $$\int_{-\beta_2}^{\beta_1} P \Phi_n(z) \Phi_m(z) dz = 0 \tag{86}$$

or since the weighing factor is constant in each region, $$P^- \int_{-\beta_2}^{0} \Phi_n(z) \Phi_m(z) dz + P^+ \int_{0}^{\beta_1} \Phi_n(z) \Phi_m(z) dz = 0. \tag{87}$$

With the eigenfunctions the above equation becomes $$P^- \cos(\lambda_n\beta_1) \cos(\lambda_m\beta_1) \int_{-\beta_2}^{0} \cos[k\lambda_{1n}(\beta_2+z)] \cos[k\lambda_{1m}(\beta_2+z)] dz + P^+ \cos(k\lambda_{1n}\beta_2) \cos(k\lambda_{1m}\beta_2) \int_{0}^{\beta_1} \cos[\lambda_{1n}(\beta_1-z)] \cos[\lambda_{1m}(\beta_1-z)] dz = 0. \tag{88}$$

The Maple software package was used to evaluate the integrals and rearrange the resulting expression to obtain $$\frac{\lambda_n \cos(\lambda_m\beta_1)\cos(k\lambda_m\beta_2)}{(\lambda_n - \lambda_m)(\lambda_n + \lambda_m)} \left[\frac{P^-}{k} \cos(\lambda_n\beta_1)\sin(k\lambda_n\beta_2) + P^+ \cos(k\lambda_n\beta_2)\sin(\lambda_n\beta_1)\right] - \frac{\lambda_m \cos(\lambda_n\beta_1)\cos(k\lambda_n\beta_2)}{(\lambda_n - \lambda_m)(\lambda_n + \lambda_m)} \left[\frac{P^-}{k} \cos(\lambda_m\beta_1)\sin(k\lambda_m\beta_2) + P^+ \cos(k\lambda_m\beta_2)\sin(\lambda_m\beta_1)\right] = 0. \tag{89}$$

The terms in [ ] become the characteristic equation and equal zero if $$P^+ = D_1, \quad 0 > z > \beta_1$$

$$P^- = D_2 k^2, \quad -\beta_2 > z > 0 \tag{90}$$

Therefore these are the weighing functions.

The last boundary condition yields the remaining undetermined constant $$C_n = \frac{\int_{-\beta_2}^{\beta_1} f(z) \Phi_n(z) dz}{\int_{-\beta_2}^{\beta_1} \Phi_n^2(z) dz}, \tag{91}$$

or

-continued $$\int_{-\beta_2}^{0} (1-\Gamma)D_2k^2\cos[k\lambda_n(\beta_2+z)]\cos(\lambda_n\beta_1)dz + \quad (92)$$

$$C_n = \frac{\int_{0}^{\beta_1} (-\Gamma)D_1\cos[\lambda_n(\beta_1-z)]\cos(k\lambda_n\beta_2)dz}{\int_{-\beta_2}^{0} D_2k^2\cos[k\lambda_n(\beta_2+z)]\cos^2(\lambda_n\beta_1)dz +}.$$

$$\int_{0}^{\beta_1} D_1\cos^2[\lambda_n(\beta_1-z)]\cos^2(k\lambda_n\beta_2)dz$$

Maple was used to evaluate these integrals and simplify the resulting algebraic equation to obtain $$C_n = \frac{2D_2k\cos(\lambda_n\beta_1)\sin(k\lambda_n\beta_2)}{\lambda_n[k^2D_2\beta_2\cos^2(\lambda_n\beta_1) + D_1\beta_1\cos^2(\lambda_n\beta_2)]}, \quad (93)$$

$$\gamma_1(x,z) = \sum_{n=1}^{\infty} -C_n\exp\left\{\frac{-\lambda_n^2 x}{Pe_1}\right\}\cos[\lambda_n(\beta_1-z)]\cos(k\lambda_n\beta_2), \quad (94)$$

and $$\gamma_2(x,z) = \sum_{n=1}^{\infty} C_n\exp\left\{\frac{-\lambda_n^2 x}{Pe_1}\right\}\cos[k\lambda_n(\beta_2+z)]\cos(\lambda_n\beta_1). \quad (95)$$

Calculation of Initial pH in Buffered Sample Stream

The foregoing calculations were modified to apply to pH (hydrogen ion concentration) measurement in an ideally buffered sample stream in which the hydrogen ion concentration in the sample stream remains unchanged.

The BC's corresponding to this case are $$\frac{\partial\gamma(\tilde{x},1)}{\partial z} = 0 \text{ (no wall flux)}, \quad (96)$$

$$\gamma(\tilde{x},0) = 0 \text{ (concentration fixed)}, \quad (97)$$

$$\gamma(0,\tilde{z}) = -\Gamma \text{ entrance.} \quad (98)$$

For this case $\tilde{x}$, $\tilde{z}$ and $P_e$ are based on the distance from the interface to the indicator side wall. The nondimensional concentration γ using these BC's is given by $$\gamma(\tilde{x},\tilde{z}) = \sum_{n=1}^{\infty} \left(\frac{-2\Gamma}{\lambda_n}\right)\exp\left(\frac{-\lambda_n^2\tilde{x}}{Pe}\right)\sin(\lambda_n\tilde{z}), \quad (99)$$

where $$\lambda_n = \frac{(2n-1)\pi}{2}, n = 1, 2, 3, \ldots \quad (100)$$

The foregoing calculations relate to systems in which the sample and indicator streams have different flow rates, viscosities and diffusivities. In cases where the flow rates, viscosities and diffusivity of the two streams are the same, it is only necessary to use the appropriate values of the input parameters in the models described above although simpler equations exist [Crank, J. (1975) *The Mathematics of Diffusion*, Eq. 2.17; Weigl, B. H. et al., Diffusion-based optical chemical detection in silicon flow structures," Analytical Methods & Instrumentation, Special Issue, MTAS 76:174–184].

This invention is described with reference to preferred embodiments; however, it will be apparent to those skilled in the art that additional equivalent procedures and devices may be substituted in the practice of this invention for those disclosed herein within the scope and spirit of applicants' contribution to the art. The appended claims are to be interpreted to include all such modifications and equivalents.

EXAMPLE 1

Calibration of Detector

In the following discussion, it is assumed that the flow speed of each stream remains constant over the time of the procedure.

A) Hardware Calibration Protocol

The light intensity distribution function (which is a combination of the spatial light output of the microscope light source and a spatial camera sensitivity response) across the channel is determined as follows:

Using neutral density filters, a video image of a T-Sensor filled with water is acquired.

The image is digitally transferred to Macintosh 8100AV using the software VideoMonitor® to generate an image file in pict-format.

Using Adobe Photoshop, the image file in pict-format is converted to tiff-format.

Using the software package NIH Image, a region in the channel (the same region in which the actual chemical measurements are going to be taken) is selected, and an intensity cross-section across the channel is determined. The resulting function usually looks like the top part of a slightly asymmetrical Gaussian distribution.

B) Chemical Calibration Protocol

A number of solutions with known concentrations of the analyte of interest are prepared using a matrix as similar as possible to the sample to be tested. Each of these solutions is then loaded into sample loops (on-chip or off-chip), and run consecutively through the T-sensor (in parallel with indicator and control streams, e.g., as described in U.S. Ser. No. 08/900,926 filed Jul. 25, 1997, incorporated herein by reference to the extent not inconsistent herewith). Then, for each calibration solution, the following procedure is applied:

A video image of T-Sensor cross-section is acquired.

The image is digitized/transferred to Macintosh 8100AV using the software VideoMonitor® to generate an image file in pict-format.

Using Adobe Photoshop, the image file in pict-format is converted to tiff-format.

Using the custom software package Imagefit, written in Matlab code, the tiff-images are processed as follows:

(a) the tiff format is converted into a matrix with each pixel represented by the following values: x-coordinate, y coordinate, red-intensity, green intensity, blue intensity;

(b) the user selects a portion of the total image, typically a 10×200 pixel area that reaches across the channel. This area contains then 10 cross-sectional "intensity slices";

(c) the user defines the color intensity to be used for the measurement (any combination of red, green and blue);

(d) the user defines certain segments across the measurement channel by defining the x-coordinate, at which each segment starts and ends. For a Reference-T-Sensor with three inlets (standard, indicator, sample), this would be: standard-background-x-start, standard-background-x-end, standard-indicator-interface-x-start, standard-indicator-interface-x-end, indicator-background-x- start, indicator-background-x-end, indicator-sample-interface-x-start, indicator-sample-interface-x-end, sample-background-x-start, sample-background-x-end.

These segments are used to derive seven measurement values as follows:

Value A: standard-background-x-start, standard-background-x-end: the intensity values are averaged and provide a measure for standard-autofluorescence or reflectivity.

Value B: standard-indicator-interface-x-start, standard-indicator-interface-x-end: The minimum or maximum intensity value or the integral between these x-values is determined and is a measure for the concentration of the analyte in the internal standard: this value serves as both a simultaneous control and internal reference value.

Value C: indicator-background-x-start, indicator-background-x-end: The intensity values are averaged and provide a measure for both the concentration variations in the indicator dye solution and for lamp intensity variations.

Value D: indicator-sample-interface-x-start, indicator-sample-interface-x-end: The minimum or maximum intensity value or the integral between these x-values is determined and is a measure for the concentration of the analyte in the sample.

Value E: sample-background-x-start, sample-background-x-end: The intensity values are averaged and provide a measure for sample-autofluorescence or reflectivity.

Value F: x-coordinate position of the maximum intensity of the standard/indicator interface: This value is a function of relative changes in both flowing volume and viscosity of the standard and the indicator stream; it is presently used as criterion for the determination of when a measurement is invalid; a second use is to determine the light intensity offset at the particular x-coordinate across the channel using the previously determined light intensity distribution function.

Value G: x-coordinate position of the maximum intensity of the sample/indicator interface; this value is a function of relative changes in both flowing volume and viscosity of the sample and the indicator stream; it is presently used as criterion for the determination of when a measurement is invalid; a second use is to determine the light intensity offset at the particular x-coordinate across the channel, using the previously determined light intensity distribution function.

Any combination of these seven values, in combination with the previously determined light intensity distribution function, can be used to derive a calibration parameter for the analyte in the sample. Typical ones would be:

| | |
|---|---|
| Conc(standard) - D | (101) |
| Conc(standard) - D/B | (102) |
| Conc(standard) - (D–E)/(B–A) | (103) |
| Conc(standard) - (D–E)/(B–A)/C | (104) |
| Conc(standard) - (D–E)/(B–A)-C | (105) |
| Conc(standard) - (D–C)/(B–C) | (106) |

If a Reference-T-Sensor with more than one internal standard and/or control is used, the equations may be modified accordingly.

Conc(analyte in standard) values derived from T-Sensor runs with calibrators and samples are then used to establish a calibration curve.

The foregoing protocol corrects the system for variations in spatial light intensity distribution of light source; spatial response function of detector (e.g., CCD camera); and inner filter effect of dye molecules (both activated states), especially for fluorescence indicators.

EXAMPLE 2

Equivalence of Alteration of Flow Rates and Particle Diffusion Patterns

Fluid Flow Rate Control: Pressure differences between inlets and outlets of the T-sensor channels were generated using adjustable water columns consisting of a set of water-filled glass tubes. For the majority of experiments a pressure drop of about 50 mm of water (5 mbar, 0.071 psi, 0.49 kPa) between all inlet and outlet ports was used. For some experiments, the pressure difference was varied between 10 mm and 150 mm to demonstrate the effect of flow rate on the sensing mechanism. Glass tubes with a diameter of 12.5 mm were used and at flow rates common in normal T-sensor operation the column widths did not change significantly during experiments. For example, for a 10 mm pressure head difference from both inlet ports to the outlet port of the T-sensor discussed herein, the sample and indicator stream delivery tube columns will fall at a rate of approximately 8 $\mu$m/min. Both sample and indicator dye introduction was achieved using a three port sample injection connector attached to the flow interface connectors. During normal operation the indicator and sample streams were injected into separate 0.28 mm ID Teflon tubing flow injection storage loops and then delivered to the T-sensor.

Optical detection: A Zeiss ICM 405 inverted microscope was equipped with a fluorescent filter set ($\lambda_{ex}$=480±10 nm, $\lambda_{em}$>510 nm) and a Zeiss 35 mm camera with 400 ASA Kodak color negative film. The silicon device was attached to the stage of the microscope with adhesive tape. Photographs were taken of the flow channel for each sample with an exposure time of 1 s. The same fluorescent filter set was used for each image and the film was developed without color or exposure correction. The photographs were scanned using a Silverscan III color scanner and converted into grayscale images using the software package Adobe Photoshop 3.0.

Sample preparation: All chemicals used were obtained from Aldrich Chemical Company, unless otherwise noted. Carboxy-SNAFL 1 (Molecular Probes, Eugene, Oreg.) was used as the indictor dye. This dye has a $pK_a$ of 7.4 and a useful dynamic range from pH 6.5 to 8.5. When excited at 480 nm it exhibits a yellow fluorescence emission for pH<6.5 and red emission in its base form with pH>8.5. The indicator dye solution was prepared in two steps. First, 1 mg of Carboxy-SNAFL 1 was dissolved in 2 ml DMSO.

The indicator stream was a mixture of 200 $\mu$l of the DMSO-Carboxy-SNAFL 1 solution with 2 ml of a 0.05 mM HEPES buffer solution of pH 5.5. For the proof-of-principle experiment a 10 mM HEPES buffer solution of pH 9.0 was used as sample. For the sample pH range experiment, samples were prepared from 10 mM HEPES buffer solutions adjusted to five pH values: 7.2, 7.4, 7.6, 7.8, and 8.0.

The pH sensitive dye (Carboxy-SNAFL 1) was used in the indicator stream. At the particular pH values used in these experiments, OH– ions and their associated cations diffuse and at equilibrium their activity will be uniform across the depth of the channel. The indicator diffuses more slowly within the channel because of its greater diffusion coefficient. Two experiments are presented: proof-of-principle results, and initial quantitative results demonstrate the precision of the detection technique.

The Effects of Flow Velocity and Diffusivity: In FIG. 3 are two fluorescence images of a 400 $\mu$m wide T-sensor detection channel operating at two different flow settings. As described above, the diffusion of OH– ions from the sample stream into the indicator stream is shown to extend a distance in the flow direction which is inversely proportional to the flow rates of the streams.

Equation 9 defines the effect of particle diffusivity and net flow rate within the T-sensor detection channel. The term $P_e=Uh/D$ reveals that an increase in net detection channel flow velocity will produce an effect that is identical to that produced by a decrease in particulate diffusivity of equal fractional magnitude. This effect is demonstrated in FIG. 3A and FIG. 3B. The pressure difference between inlet and outlet ports was 30 mm water for the experiment shown in FIG. 3A, and 70 mm pressure differential was used for the experiment in FIG. 3B. The pressure differential between the inlet and the outlet port of the experiment shown in FIG. 3B is approximately 2.3 times (70 mm/30 mm) that of the experiment shown in FIG. 3A resulting in a detection channel flow rate increase of 2.3 times as well. The reduced movement of the interface into the detection channel at corresponding axial locations follows immediately from this increase in the net detection channel flow rate, as expected.

EXAMPLE 3
Analytical Model for pH Determination

In the study used to generate FIGS. 4 and 5, pH (hydrogen ion concentration) of the sample stream was determined using a pH sensitive dye in the indicator stream. As pH active ions diffused from the sample stream into the indicator stream, the pH of the indicator stream changed causing a color change in the dye. The loci of the points of known concentration along the line of color change (FIG. 3) were used with the analytical model of the diffusion process of this invention to determine the entering sample stream ion concentration (pH).

A T-sensor was used as described in Weigl, B. H., et al. (1996), "Diffusion-based optical chemical detection in silicon flow structures," Analytical Methods and Instrumentation, Special $\mu$TAS'96:174–184. The channel widths were 50 $\mu$m. The channel depth (diffusion direction) was 0.4 mm. The length of the flow channel was 15 mm.

The flow rates through the T-sensor were controlled by adjusting column heights of the inlet and outlet streams of the sensor. An average pressure drop of 30 mm of water existed across the test section. The approximate average velocity for both the sample and indicator streams of 2.4 mm/s in the channel was calculated using this pressure drop based on Poiseuille flow in a slot $$U = \frac{b^2}{3\mu}\frac{dp}{dx}. \quad (107)$$

Carboxy-SNAFL 1 (Molecular Probes, Eugene, Oreg.) was the indicator dye. This dye has a dynamic range from pH 6.5 to 8.5, and a $pK_a$ of 7.4. The indicator solution was prepared by dissolving 1 mg of SNAFL in 2 ml of DMSO. Then 200 $\mu$L of the DMSO-SNAFL solution was mixed with 2 ml of 0.05 mM HEPES buffer to obtain an indicator solution of pH 5.5. The sample stream was a 10 mM HEPES buffer solution at pH 9.0.

In the case of pH the diffusing species are the ions $[H^+]$ and $[OH^-]$. The more slowly than these ions. Therefore the diffusion of $[H^+]$ and $[OH^-]$ was assumed to control the reaction, bringing the ions to the other species (Olmsted, J. III and Williams, G. M., *Chemistry The Molecular Science*, Mosby, St. Louis 1994). Thus the model was applied to hydroxide ion diffusion from the sample stream ($D_{OH^-}$= 5.27×10$^{-5}$ cm$^2$/s [Lide, D. R., *CRC Handbook of Chemistry and Physics*, CRC Press, Boca Raton 1994]).

A 35 mm color image was made through a Zeiss ICM 405 inverted microscope equipped with a fluorescent filter set ($I_{ex}$=480 nm, $I_{em}$=510 nm). The magnification was approximately 2.5×, and the exposure time was approximately 1 second. The sample stream entered the channel from the bottom left and the indicator stream entered the channel from the bottom right. Both streams exited at the top. A yellow/red transition line indicated the transition of the pH sensitive dye. Based on the $pK_a$ and dynamic range of the dye, the transition line was taken as the location where pH=7.4±0.5.

Nine locations on the pH transition line were plotted along with isoconcentration lines calculated from both the unbuffered and buffered models as shown in FIGS. 4 and respectively. The non-dimensionalization in each case was different because the flow rates were not exactly equal, $$h_{unbuffered}=180\ \mu m,\ h_{buffered}=230\ \mu m. \quad (108)$$

The average velocity for each stream was approximately equal to that calculated in the above equation, resulting in $$Pe_{unbuffered}=84,\ Pe_{buffered}=105. \quad (109)$$

For each experimental point in FIGS. 4 and 5 a value of $\gamma$ was calculated yielding average values $$\gamma=-0.37\ \text{unbuffered},\ \gamma=-0.989\ \text{buffered}. \quad (110)$$

Finally the entering sample stream ion concentration was calculated using the equation:

$$\gamma=(c-c_{eq})/c_0 \quad (111)$$

$$[OH^-]=2.39\times10^{-6}\ M \Rightarrow pH=8.38\pm0.16\ \text{unbuffered}. \quad (112)$$

$$[OH^-]=2.40\times10^{-5}\ M \Rightarrow pH=9.38\pm0.16\ \text{buffered}. \quad (113)$$

Note in the above calculations for the unbuffered case $c_{eq}$ is related to $c_0$ by the dimensions of each stream whereas for the ideally buffered case $c_{eq}=c_0$.

These pH estimates bracket the pH of the sample (9.0). The buffered model overestimated the sample stream pH. The effect of buffering in the model causes a high calculation of $[OH^-]$ in the indicator stream, compared to a partially buffered situation. The overestimation of hydroxide ion concentration resulted in an underestimation of hydrogen ion concentration and therefore a high calculation of pH. The unbuffered model underestimated the sample stream pH. the unbuffered model calculated a lower $[OH^-]$ in the indicator stream than a partially buffered situation. This resulted in a high estimate of hydrogen ion concentration and therefore a low calculation of pH.

These results indicate that the sample stream was not in fact fully buffered or fully unbuffered. In order to investigate this possibility, sample and indicator solutions with approximately the same buffering as the case described above were mixed and the pH measured using a pH electrode. This measurement showed a change in pH but less than that for an unbuffered case. Therefore the system was not fully buffered but rather partially buffered.

This invention is described with reference to preferred embodiments; however, it will be apparent to those skilled in the art that additional equivalent procedures and devices may be substituted in the practice of this invention for those disclosed herein within the scope and spirit of applicants' contribution to the art. The appended claims are to be interpreted to include all such modifications and equivalents.

We claim:

1. A method for determining the initial concentration of diffusible analyte particles in a sample stream entering a laminar flow channel of known dimensions in laminar flow relative to an indicator stream containing an indicator substance capable of exhibiting a detectable change at a known concentration of said diffusible analyte particles, comprising:

(a) determining the flow ratio of said streams and diffusivity ratio of said analyte particles in said streams;

(b) selecting detection points in said indicator stream where said indicator substance exhibits a detectable change indicative of a particular concentration of said diffusible analyte particles at said detection point;

(c) using said known concentration of diffusible analyte particles at said detection points and the locations of said detection points to determine the initial concentration of said diffusible analyte particles in said sample stream.

2. The method of claim 1 also comprising determining the diffusivity of said indicator substance in said sample stream and determining the local concentration of said indicator substance at each of said detection points and using said local concentrations of indicator substance to calculate the concentrations of said diffusible analyte particles at each of said detection points.

3. The method of claim 1 wherein the viscosities of said sample and indicator streams are substantially equal.

4. The method of claim 1 wherein the flow rates of said sample and indicator streams are substantially equal.

5. The method of claim 1 wherein the flow rates of said sample and indicator streams are not substantially equal.

6. The method of claim 1 wherein the viscosities of said sample and indicator streams are not substantially equal, also comprising determining the viscosities of said sample and indicator streams.

7. The method of claim 1 wherein said viscosities are calculated in a method comprising determining the position of the interface between said sample stream and said indicator stream.

8. The method of claim 1 wherein said detectable change in said indicator substance is detected by an optical instrument.

9. The method of claim 8 wherein specific response values of said optical instrument are correlated with known concentrations of said analyte particles in said indicator stream.

10. The method of claim 1 wherein said laminar flow channel has an aspect ratio less than about ¼.

11. A method for generating reference data relating positions of points of known concentration of diffusible analyte particles in an indicator stream comprising an indicator substance capable of exhibiting a detectable change at a known concentration of said diffusible analyte particles, in laminar flow with a sample stream, to initial concentrations of said analyte particles in said sample stream, comprising:

(a) providing a laminar flow channel of known dimensions;

(b) providing flow rates for said streams and diffusivities of said analyte particles in said streams;

(c) providing a concentration of said analyte particles in said indicator stream correlated to a specific detectable change in said indicator substance;

(d) calculating the positions of points of said specific detectable change in said indicator substance which would result from different initial concentrations of said analyte particles in said sample stream.

12. The method of claim 11 also comprising providing the position of the centerline of said flow channel, the position of a point on the interface between the indicator and sample streams, and the distance of said point from said centerline.

13. The method of claim 11 also comprising providing the viscosities of said sample stream and said indicator stream.

14. The method of claim 11 also comprising providing the diffusivity of said indicator substance in said sample stream.

15. The method of claim 11 wherein said laminar flow channel has an aspect ratio of less than about ¼.

16. The method of claim 11 also comprising calculating the initial concentration of said diffusible analyte particles in a test sample stream comprising the steps:

(a) introducing said test sample stream and said indicator stream into said laminar flow channel in laminar flow at said flow rates;

(b) detecting the position of at least one point of detectable change of said indicator substance in said indicator stream;

(c) comparing the detected position of step (b) with said reference data to determine the initial concentration of said diffusible analyte particles in said test sample stream corresponding to said detected position.

17. The method of claim 16 wherein said calculating and comparing steps are performed by computer.

18. An apparatus for determining the initial concentration of diffusible analyte particles in a sample stream comprising:

(a) a laminar flow channel of known dimensions for introduction of said sample stream in laminar flow with an indicator stream containing an indicator substance capable of exhibiting a detectable change at a known concentration of said diffusible analyte particles;

(b) means for determining the flow rates of said streams in said flow channel whereby said flow rates are known;

(c) means for detecting a change in said indicator substance at a selected detection point of known coordinates in said indicator stream, said change being indicative of a particular concentration of said diffusible analyte particles at said detection point;

(d) computerized means for calculating the initial concentration of said diffusible analyte particles in said sample stream using said known channel dimensions, known flow rates, and known coordinates.

* * * * *

UNITED STATES PATENT AND TRADEMARK OFFICE
CERTIFICATE OF CORRECTION

PATENT NO. : 5,974,867

DATED : November 2, 1999

INVENTOR(S) : Forster et al.

It is certified that error appears in the above-identified patent and that said Letters Patent is hereby corrected as shown below:

In column 8, line 17, delete the word "actual".

In column 9, line 55, delete "In the embodiment shown" and replace with --In an embodiment not shown--.

In column 9, line 58, delete the word "at" and replace with --to form a-- and insert a period following the word "area".

In column 9, line 58, delete "120; however devices with shorter flow channels may also be used in this invention."

In column 11, line 25, delete the word "actual".

In column 11, line 35, delete the word "white".

In column 11, line 36, insert --is-- between "T-sensor" and "driven".

In column 11, line 46, delete "the detection channel T-joint 58 from the right inlet channel 50" and replace with --interface 120--.

In column 11, line 48, delete "appears as a dark (clear) fluid" and replace with --is shown as a densely hatched area--.

In column 11, line 50, delete "in indicator stream inlet channel 40" and insert a period following the word "left".

In column 11, line 53, delete "light gray area 130" and replace with --white area 85--.

In column 11, line 54, delete "dark gray area 140" and replace with --hatched area 90--.

In column 11, line 61, delete "130" and replace with --95--.

UNITED STATES PATENT AND TRADEMARK OFFICE
CERTIFICATE OF CORRECTION

PATENT NO. : 5,974,867

DATED : November 2, 1999

INVENTOR(S) : Forster et al.

It is certified that error appears in the above-identified patent and that said Letters Patent is hereby corrected as shown below:

In column 14, line 55, delete "Pe2" and replace with --$Pe_2$--.

In column 16, line 48, delete "h.Pe$_1$" and replace with --h·$Pe_1$--.

Please replace equations (10) and (11) in column 17 with the following equations:

$$\frac{\partial^2 u_1}{\partial z^2} + \frac{\partial^2 u_1}{\partial y^2} = \left(\frac{1}{\mu_1}\right)\left(\frac{dP}{dx}\right) \tag{10}$$

and $$\frac{\partial^2 u_2}{\partial z^2} + \frac{\partial^2 u_2}{\partial y^2} = m12\left(\frac{1}{\mu_1}\right)\left(\frac{dP}{dx}\right), \tag{11}$$

Please replace equations (13) and (14) in column 18 with the following equations:

$$\frac{\partial^2 u_1}{\partial z^2} + \frac{\partial^2 u_1}{\partial y^2} = 1 \tag{13}$$

$$\frac{\partial^2 u_1}{\partial z^2} + \frac{\partial^2 u_2}{\partial y^2} = m12 \tag{14}$$

UNITED STATES PATENT AND TRADEMARK OFFICE
CERTIFICATE OF CORRECTION

PATENT NO. : 5,974,867

DATED : November 2, 1999

INVENTOR(S) : Forster et al.

It is certified that error appears in the above-identified patent and that said Letters Patent is hereby corrected as shown below:

Please insert --no slip-- and the end of equation (15) in column 18, at about line 23.

Please replace equations (30) and (31) in column 19 with the following equations:

and
$$v_1(y,z) = [D_1 \cosh(\lambda_1 y) + E_1 \sin h(\lambda_1 y)] \cdot [B_1 \cos(\lambda_1 z) + C_1 \sin(\lambda_1 z)] \quad (30)$$

$$v_2(y,z) = [D_2 \cosh(\lambda_2 y) + E_2 \sin h(\lambda_2 y)] \cdot [B_2 \cos(\lambda_2 z) + C_2 \sin(\lambda_2 z)], \quad (31)$$

Please replace equation (33) in column 19 with the following equation:

$$\sin(\alpha-\beta) = \sin\alpha\cos\beta - \cos\alpha\sin\beta \qquad \sin(\alpha+\beta) = \sin\alpha\cos\beta + \cos\alpha\sin\beta \quad (33)$$

Please insert a period at the end of equation (36) following "=0" in column 20.

Please delete "=0" in equation (66) in column 22.

Please insert a period at the end of equation (84) following "=0" in column 23.

Please replace equation (85) in column 24 with the following equation:

$$\Phi_n(z) = \cos(k\lambda_{1n}\beta_2)\cos[\lambda_{1n}(\beta_1 - z)], \quad 0 < z < \beta_1$$
$$= \cos(\lambda_{1n}\beta_1)\cos[k\lambda_{1n}(\beta_2 + z)], \quad -\beta_2 < z < 0 \quad (85)$$

UNITED STATES PATENT AND TRADEMARK OFFICE
CERTIFICATE OF CORRECTION

PATENT NO. : 5,974,867

DATED : November 2, 1999

INVENTOR(S) : Forster et al.

It is certified that error appears in the above-identified patent and that said Letters Patent is hereby corrected as shown below:

Please replace equation (90) in column 24 with the following equation:

$$P^+ = D_1, \quad 0 < z < \beta_1 \qquad (90)$$
$$P^- = D_2 k^2, \quad -\beta_2 < z < 0$$

Please replace equation (92) in column 25 with the following equation:

$$C_n = \frac{\int_{-\beta_2}^{0}(1-\Gamma)D_2 k^2 \cos[k\lambda_n(\beta_2+z)]\cos(\lambda_n\beta_1)dz + \int_{0}^{\beta_1}(-\Gamma)D_1\cos[\lambda_n(\beta_1-z)]\cos(k\lambda_n\beta_2)dz}{\int_{-\beta_2}^{0}D_2 k^2 \cos^2[k\lambda_n(\beta_2+z)]\cos^2(\lambda_n\beta_1)dz + \int_{0}^{\beta_1}D_1\cos^2[\lambda_n(\beta_1-z)]\cos^2(k\lambda_n\beta_2)dz} \qquad (92)$$

In column 29, line 62, insert --indicator dye and any other constituents in the sample or indicator streams diffuse much-- after "[OH⁻]. The".

In column 30, line 16, insert --5-- following "FIGS. 4 and".

Signed and Sealed this

Eighteenth Day of July, 2000

Attest:

Q. TODD DICKINSON

*Attesting Officer*     *Director of Patents and Trademarks*